US012747438B2

(12) United States Patent
Fu et al.

(10) Patent No.: US 12,747,438 B2
(45) Date of Patent: Sep. 29, 2026

(54) COMPOSITIONS AND METHODS FOR REPROGRAMMING AGE-RESTRICTED NON-NEURONAL CELLS

(71) Applicant: The Regents of the University of California, Oakland, CA (US)

(72) Inventors: Xiang-Dong Fu, Rancho Santa Fe, CA (US); Hao Qian, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1207 days.

(21) Appl. No.: 17/767,045

(22) PCT Filed: Oct. 9, 2020

(86) PCT No.: PCT/US2020/054940

§ 371 (c)(1),
(2) Date: Apr. 6, 2022

(87) PCT Pub. No.: WO2021/072163

PCT Pub. Date: Apr. 15, 2021

(65) Prior Publication Data

US 2022/0364091 A1 Nov. 17, 2022

Related U.S. Application Data

(60) Provisional application No. 62/913,104, filed on Oct. 9, 2019.

(51) Int. Cl.

| | |
|---|---|
| ***C12N 15/113*** | (2010.01) |
| ***A61K 31/7105*** | (2006.01) |
| ***A61K 45/06*** | (2006.01) |
| ***C12N 15/86*** | (2006.01) |

(52) U.S. Cl.

CPC ........ *C12N 15/113* (2013.01); *A61K 31/7105* (2013.01); *A61K 45/06* (2013.01); *C12N 15/86* (2013.01); *C12N 2310/141* (2013.01); *C12N 2310/531* (2013.01); *C12N 2320/31* (2013.01); *C12N 2750/14143* (2013.01)

(58) Field of Classification Search

CPC ................ A61K 31/7105; C12N 15/86; C12N 2310/141; C12N 2310/531

See application file for complete search history.

(56) References Cited

U.S. PATENT DOCUMENTS

| | | | | |
|---|---|---|---|---|
| 2006/0105360 | A1 | 5/2006 | Croce et al. | |
| 2015/0037299 | A1 | 2/2015 | Brodie et al. | |
| 2017/0247767 | A1* | 8/2017 | Lu | C12Q 1/708 |
| 2019/0119673 | A1 | 4/2019 | Fu et al. | |

FOREIGN PATENT DOCUMENTS

| | | | | |
|---|---|---|---|---|
| WO | WO-2014071157 A1 * | 5/2014 | | A61K 45/06 |
| WO | 2017/218551 A1 | 12/2017 | | |
| WO | 2018/049226 A1 | 3/2018 | | |

OTHER PUBLICATIONS

Li, Qian, et al. "Reducing polypyrimidine tract-binding protein 1 fails to promote neuronal transdifferentiation on HT22 and mouse astrocyte cells under physiological conditions." Experimental and Therapeutic Medicine 27.2 (2023): 72. (Year: 2023).*

Uhlik, M. T., Temple, B., Bencharit, S., Kimple, A. J., Siderovski, D. P., & Johnson, G. L. (2005). Structural and evolutionary division of phosphotyrosine binding (PTB) domains. Journal of molecular biology, 345(1), 1-20. (Year: 2005).*

Yan, K. S., Kuti, M., & Zhou, M. M. (2002). PTB or not PTB—that is the question. FEBS letters, 513(1), 67-70. (Year: 2002).*

Liang, Xin, et al. "Inhibition of polypyrimidine tract-binding protein 3 induces apoptosis and cell cycle arrest, and enhances the cytotoxicity of 5-fluorouracil in gastric cancer cells." British journal of cancer 116.7 (2017): 903-911. (Year: 2017).*

Wang, Xue-jun, et al. "A simple and robust vector-based shRNA expression system used for RNA interference." PloS one 8.2 (2013): e56110. (Year: 2013).*

Engel, M., Do-Ha, D., Munoz, S. S., & Ooi, L. (2016). Common pitfalls of stem cell differentiation: a guide to improving protocols for neurodegenerative disease models and research. Cellular and Molecular Life Sciences, 73(19), 3693-3709. (Year: 2016).*

Baharlou, Simin, International Preliminary Report on Patentability and Written Opinion, PCT/US2020/054940, The International Bureau of WIPO, Apr. 21, 2022.

Young, Lee, International Search Report and Written Opinion, PCT/US2020/054940, International Searching Authority, United States Patent and Trademark Office, Mar. 1, 2021.

* cited by examiner

*Primary Examiner* — Jennifer Dunston
*Assistant Examiner* — Christina Tran
(74) *Attorney, Agent, or Firm* — McKee, Voorhees & Sease, PLC

(57) ABSTRACT

Provided herein are compositions and methods for reprogramming a non-neuronal cell to a neuron. Aspects of the present disclosure relate to compositions and methods for transdifferentiating an age-restricted non-neuronal cell into a neuron. Also provided herein is a method of treating neurodegenerative disease by reprogramming region or anatomy specific non-neuronal cells into specific types of functionalized neurons.

3 Claims, 11 Drawing Sheets

Specification includes a Sequence Listing.

cagctgcgcgctcgctcgctcactgaggccgcccgggcaaagcccgggcgtcgggcgacctttggtcgcccggcctcagtgagcgagcg
agcgcgcagagagggagtggccaactccatcactaggggttccttgtagttaatgattaacccgccatgctacttatctacgtacattat
attggctcatgtccaacattaccgccatgttgacattgattattgactagttattaatagtaatcaattacggggtcattagttcatagccca
tatatggagttccgcgttacataacttacggtaaatggcccgcctggctgaccgcccaacgacccccgcccattgacgtcaataatgacgt
atgttcccatagtaacgccaatagggactttccattgacgtcaatgggtggagtatttacggtaaactgcccacttggcagtacatcaagt
gtatcatatgccaagtacgccccctattgacgtcaatgacggtaaatggcccgcctggcattatgcccagtacatgaccttatgggactttc
ctacttggcagtacatctacgtattagtcatcgctattaccatggtgatgcggttttggcagtacatcaatgggcgtggatagcggtttgac
tcacggggatttccaagtctccaccccattgacgtcaatgggagtttgttttggcaccaaaatcaacgggactttccaaaatgtcgtaaca
actccgccccattgacgcaaatgggcggtaggcgtgtacggtgggaggtctatataagcagagctcgtttagtgaaccgtcagatcgcct
ggagacgccatccacgctgttttgacctccatagaagacaccgggaccgatccagcctcccctcgaagctttacatgtggtacccttcagg
tcgacatttatccctaaacaggataacactagcataacttcgtataggatactttatacgaagttattcgcgatgaataaatgaaagcttg
cagatctgcgactctagaggatctgcgactctagaggatcataatcagccataccacatttgtagaggttttacttgctttaaaaaacctc
ccacacctccccctgaacctgaaacataaaatgaatgcaattgttgttgttaacttgtttattgcagcttataatggttacaaataaagcaa
tagcatcacaaatttcacaaataaagcatttttttcactgcattctagttgtggtttgtccaaactcatcaatgtatcttatcatgtctggatc
tgcgactctagaggatcataatcagccataccacatttgtagaggttttacttgctttaaaaaacctcccacacctccccctgaacctgaaa
cataaaatgaatgcaattgttgttgttaacttgtttattgcagcttataatggttacaaataaagcaatagcatcacaaatttcacaaataa
agcatttttttcactgcattctagttgtggtttgtccaaactcatcaatgtatcttatcatgtctggatctgcgactctagaggatcataatca
gccataccacatttgtagaggttttacttgctttaaaaaacctcccacacctccccctgaacctgaaacataaaatgaatgcaattgttgtt
gttaacttgtttattgcagcttataatggttacaaataaagcaatagcatcacaaatttcacaaataaagcatttttttcactgcattctagt
tgtggtttgtccaaactcatcaatgtatcttatcatgtctggatccccatcaagctgatccggaacccttaatataacttcgtataggatact
tttatacgaagttattagctagttacagtaccggcttagttaggaattgccaccatgagcgagctgatcaaggagaacatgcacatgaagc
tgtacatggagggcaccgtgaacaaccacttcaagtgcacatccgagggcgaaggcaagccctacgagggcacccagaccatgaa L-ITR
CMV
Loxp
Loxp
RFP

FIG. 7 gatcaaggtggtcgagggcggccctctcccccttcgccttcgacatcctggctaccagcttcatgtacggcagcaaagccttcatcaaccac
acccagggcatccccgacttctttaagcagtccttccctgagggcttcacatgggagagaatcaccacatacgaagacgggggcgtgctg — RFP
accgctacccaggacaccagcttccagaacggctgcatcatctacaacgtcaagatcaacggggtgaacttcccatccaacggccctgtg
atgcagaagaaaacacgcggctgggaggccaacaccgagatgctgtaccccgctgacggcggcctgagaggccacagccagatggcc
ctgaagctcgtgggcgggggctacctgcactgctccttcaagaccacatacagatccaagaaacccgctaagaacctcaagatgcccgg
cttccacttcgtggaccacagactggaaagaatcaaggaggccgacaaagagacctacgtcgagcagcacgagatggctgtggccaag
tactgcgacctccctagcaaactggggcacagataatcgatagtttgtttgaatgaggcttcagtactttacagaatcgttgcctgcacatc
ttggaaacacttgctgggattacttcttcaggttaacccaacagaaggcTCGAGAAGGTATATTGCTGTTGACAGTGAGCG — ShPTB
AGGGTGAAGATCCTGTTCAATATAGTGAAGCCACAGATGTATATTGAACAGGATCTTCACCCGTGCCTA
ACTG CCTCGGaattcGTGGAAAG GACGAAACACCGGGGTGAAGATCCTGTTCAATACTCGAGTATTGAAC — ShPTB
AGGATCTTCACCCTTTTTGAATTAATGGCAACTCTGACAGATGTGGCGGGAGGAAAGCTGAGGTGGGA
GTACTGCTCAGAGCTACAACTCTAGGAGTAGGGACTCCAAGCCTAGAGCTCCAAGAGAGGGTGAAGGG
CAGGGAGAAAATTATAGTAATAGTTGCAATGAGTCACTTGCTTCTAGATCAAGATCAGAGACTCTGCTCT — miR124
OCGTGTTCACAGCGGACCTTGATTTAATGTCATACAATTAAGGCACGCGGTGAATGCCAAGAGCG GAGC
CTACAGCTGCACTTGAAGGACATCCGAGAGAAGTTAGGAAGGGTGGGGAGAAACAATTCTAGAATGAA
CCCATCCTGTGCGACACAAGGACCCCTCGCATTGATTCAAAATCTTTAGAATACAAGACAGTCAAActgtc
ggtcccctctggctctccgcgtgcgcccggggctgcgggagcggagtccgctcaggcccccgcgccgggtcggcggcggcacgtggggc
ccacagcgcggcagcggtgccggcgaatgggaggcccgtttctctctttggttatctagctgtatgagtgccacagagccgtcataaagct — miR9
agataaccgaaagtagaaatgactctcacaacttctgcgtgcgatggcccggccggccgccctggccacaggagccagaggagcccag
agaagcccacgccacccagggattccagctcgacggagcggccacgccgggaccaggtatccgacctcggctctccaattctaaatttc
gaaagtcgacgtcggttggcgcgccagctcgcgccagctatcaagctcgagTgctttatttgtgaaatttgtgatactattgctttatttgta
accattataagctgcaataaacaagttaacaacaacaattgcattcattttatgtttcaggttcagggggaggtgtgggaggttttttaaa

FIG. 7 (Continued)

ggggagggggtacgtagataagtagcatggcgggttaatcattaactacaaggaacccctagtgatggagttggccactccctctctgc
gcgctcgctcgctcactgaggccgggcgaccaaaggtcgcccgacgcccgggctttgcccgggcggcctcagtgagcgagcgagcgcgc R-ITR
cagctggcgtaatagcgaagaggcccgcaccgatcgcccttcccaacagttgcgcagcctgaatggcgaatggcgattctgttgcaatgg
ctggcggtaatattgttctggatattaccagcaaggccgatagtttgagttcttctactcaggcaagtgatgttattactaatcaaagaagt
attgcgacaacggttaatttgcgtgatggacagactcttttactcggtggcctcactgattataaaaacacttctcaggattctggcgtacc
gttcctgtctaaaatccctttaatcggcctcctgtttagctcccgctctgattctaacgaggaaagcacgttatacgtgctcgtcaaagc
ccatagtacgcgccctgtagcggcgcattaagcgcggcgggtgtggtggttacgcgcagcgtgaccgctacacttgccagcgccctagcg
cccgctcctttcgctttcttcccttcctttctcgccacgttcgccggctttccccgtcaagctctaaatcgggggctccctttagggttccgatt
tagtgctttacggcacctcgaccccaaaaaacttgattagggtgatggttcacgtagtgggccatcgccctgatagacggtttttcgccctt
tgacgttggagtccacgttctttaatagtggactcttgttccaaactggaacaacactcaaccctatctcggtctattcttttgatttataagg
gattttgccgatttcggcctattggttaaaaaatgagctgatttaacaaaaatttaacgcgaattttaacaaaatattaacgtttacaattt
aaatatttgcttatacaatcttcctgtttttggggcttttctgattatcaaccggggtacatatgattgacatgctagttttacgattaccgttc
atcgattctcttgtttgctccagactctcaggcaatgacctgatagcctttgtagagacctctcaaaaatagctaccctctccggcatgaatt
tatcagctagaacggttgaatatcatattgatggtgatttgactgtctccggcctttctcacccgtttgaatctttacctacacattactcagg
cattgcatttaaaatatatgagggttctaaaaatttttatccttgcgttgaaataaaggcttctcccgcaaaagtattacagggtcataatg
tttttggtacaaccgatttagctttatgctctgaggctttattgcttaattttgctaattctttgccttgcctgtatgatttattggatgttggaat
gccctgatgcggtattttctccttacgcatctgtgcggtatttcacaccgcatatggtgcactctcagtacaatctgctctgatgccgcatag
ttaagccagccccgacacccgccaacacccgctgacgcgccctgacgggcttgtctgctcccggcatccgcttacagacaagctgtgacc
gtctccgggagctgcatgtgtcagaggttttcaccgtcatcaccgaaacgcgcgagacgaaagggcctcgtgatacgcctatttttatagg
ttaatgtcatgataataatggtttcttagacgtcaggtggcacttttcggggaaatgtgcgcggaacccctatttgtttatttttctaaataca
ttcaaatatgtatccgctcatgagacaataaccctgataaatgcttcaataatattgaaaaaggaagagtatgagtattcaacatttccgt
gtcgcccttattcccttttttgcggcattttgccttcctgtttttgctcacccagaaacgctggtgaaagtaaaagatgctgaagatcagttg
ggtgcacgagtgggttacatcgaactggatctcaacagcggtaagatccttgagagttttcgccccgaagaacgttttccaatgatgagc

FIG. 7 (Continued)

acttttaaagttctgctatgtggcgcggtattatcccgtattgacgccgggcaagagcaactcggtcgccgcatacactattctcagaatga
cttggttgagtactcaccagtcacagaaaagcatcttacggatggcatgacagtaagagaattatgcagtgctgccataaccatgagtga
taacactgcggccaacttacttctgacaacgatcggaggaccgaaggagctaaccgcttttttgcacaacatgggggatcatgtaactcg
ccttgatcgttgggaaccggagctgaatgaagccataccaaacgacgagcgtgacaccacgatgcctgtagcaatggcaacaacgttgc
gcaaactattaactggcgaactacttactctagcttcccggcaacaattaatagactggatggaggcggataaagttgcaggaccacttc
tgcgctcggcccttccggctggctggtttattgctgataaatctggagccggtgagcgtgggtctcgcggtatcattgcagcactggggcca
gatggtaagccctcccgtatcgtagttatctacacgacggggagtcaggcaactatggatgaacgaaatagacagatcgctgagatagg
tgcctcactgattaagcattggtaactgtcagaccaagtttactcatatatactttagattgatttaaaacttcatttttaatttaaaaggatc
taggtgaagatcctttttgataatctcatgaccaaaatcccttaacgtgagttttcgttccactgagcgtcagaccccgtagaaaagatca
aaggatcttcttgagatcctttttttctgcgcgtaatctgctgcttgcaaacaaaaaaaccaccgctaccagcggtggtttgtttgccggatc
aagagctaccaactctttttccgaaggtaactggcttcagcagagcgcagataccaaatactgtccttctagtgtagccgtagttaggcca
ccacttcaagaactctgtagcaccgcctacatacctcgctctgctaatcctgttaccagtggctgctgccagtggcgataagtcgtgtctta
ccgggttggactcaagacgatagttaccggataaggcgcagcggtcgggctgaacggggggttcgtgcacacagcccagcttggagcg
aacgacctacaccgaactgagatacctacagcgtgagctatgagaaagcgccacgcttcccgaagggagaaaggcggacaggtatcc
ggtaagcggcagggtcggaacaggagagcgcacgagggagcttccagggggaaacgcctggtatctttatagtcctgtcgggtttcgcc
acctctgacttgagcgtcgatttttgtgatgctcgtcaggggggcggagcctatggaaaaacgccagcaacgcggcctttttacggttcct
ggccttttgctggccttttgctcacatgttctttcctgcgttatcccctgattctgtggataaccgtattaccgcctttgagtgagctgataccg
ctcgccgcagccgaacgaccgagcgcagcgagtcagtgagcgaggaagcggaagagcgcccaatacgcaaaccgcctctccccgcgc
gttggccgattcattaatg FIG. 7
(Continued)

SEQUENCE LISTING

<160> NUMBER OF SEQ ID NOS: 8

<210> SEQ ID NO 1
<211> LENGTH: 7587
<212> TYPE: DNA
<213> ORGANISM: Artificial Sequence
<220> FEATURE:
<223> OTHER INFORMATION: Vector AAV-mshPTB-124-9

<400> SEQUENCE: 1
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac gtacatttat 180
attggctcat gtccaacatt accgccatgt tgacattgat tattgactag ttattaatag 240
taatcaatta cggggtcatt agttcatagc ccatatatgg agttccgcgt tacataactt 300
acggtaaatg gcccgcctgg ctgaccgccc aacgaccccc gcccattgac gtcaataatg 360
acgtatgttc ccatagtaac gccaataggg actttccatt gacgtcaatg ggtggagtat 420
ttacggtaaa ctgcccactt ggcagtacat caagtgtatc atatgccaag tacgccccct 480
attgacgtca atgacggtaa atggcccgcc tggcattatg cccagtacat gaccttatgg 540
gactttccta cttggcagta catctacgta ttagtcatcg ctattaccat ggtgatgcgg 600
ttttggcagt acatcaatgg gcgtggatag cggtttgact cacggggatt tccaagtctc 660
caccccattg acgtcaatgg gagtttgttt tggcaccaaa atcaacggga ctttccaaaa 720
tgtcgtaaca actccgcccc attgacgcaa atgggcggta ggcgtgtacg gtgggaggtc 780
tatataagca gagctcgttt agtgaaccgt cagatcgcct ggagacgcca tccacgctgt 840
tttgacctcc atagaagaca ccgggaccga tccagcctcc cctcgaagct ttacatgtgg 900
tacccttcag gtcgacattt atccctaaac aggataacac tagcataact tcgtatagga 960
tactttatac gaagttattc gcgatgaata aatgaaagct tgcagatctg cgactctaga 1020
ggatctgcga ctctagagga tcataatcag ccataccaca ttttgtagag gttttacttg 1080
ctttaaaaaa cctcccacac ctccccctga acctgaaaca taaaatgaat gcaattgttg 1140
ttgttaactt gtttattgca gcttataatg gttacaaata aagcaatagc atcacaaatt 1200
tcacaaataa agcatttttt tcactgcatt ctagttgtgg tttgtccaaa ctcatcaatg 1260
tatcttatca tgtctggatc tgcgactcta gaggatcata atcagccata ccacatttgt 1320
agaggtttta cttgctttaa aaaacctccc acacctcccc ctgaacctga aacataaaat 1380
gaatgcaatt gttgttgtta acttgtttat tgcagcttat aatggttaca aataaagcaa 1440
tagcatcaca aatttcacaa ataaagcatt tttttcactg cattctagtt gtggtttgtc 1500
caaactcatc aatgtatctt atcatgtctg gatctgcgac tctagaggat cataatcagc 1560
cataccacat ttgtagaggt tttacttgct ttaaaaaacc tcccacacct ccccctgaac 1620
ctgaaacata aaatgaatgc aattgttgtt gttaacttgt ttattgcagc ttataatggt 1680
tacaaataaa gcaatagcat cacaaatttc acaaataaag catttttttc actgcattct 1740
agttgtggtt tgtccaaact catcaatgta tcttatcatg tctggatccc catcaagctg 1800
atccggaacc cttaatataa cttcgtatag gatactttat acgaagttat tagctagtta 1860
cagtaccggc ttagttagga attgccacca tgagcgagct gatcaaggag aacatgcaca 1920
tgaagctgta catggagggc accgtgaaca accaccactt caagtgcaca tccgagggcg 1980
aaggcaagcc ctacgagggc acccagacca tgaagatcaa ggtggtcgag ggcggccctc 2040
tccccttcgc cttcgacatc ctggctacca gcttcatgta cggcagcaaa gccttcatca 2100
accacaccca gggcatcccc gacttcttta agcagtcctt ccctgagggc ttcacatggg 2160
agagaatcac cacatacgaa gacgggggcg tgctgaccgc tacccaggac accagcttcc 2220
agaacggctg catcatctac aacgtcaaga tcaacggggt gaacttccca tccaacggcc 2280
ctgtgatgca gaagaaaaca cgcggctggg aggccaacac cgagatgctg taccccgctg 2340
acggcggcct gagaggccac agccagatgg ccctgaagct cgtgggcggg ggctacctgc 2400
actgctcctt caagaccaca tacagatcca agaaacccgc taagaacctc aagatgcccg 2460
gcttccactt cgtggaccac agactggaaa gaatcaagga ggccgacaaa gagacctacg 2520
tcgagcagca cgagatggct gtggccaagt actgcgacct ccctagcaaa ctggggcaca 2580
gataatcgat agtttgtttg aatgaggctt cagtacttta cagaatcgtt gcctgcacat 2640
cttggaaaca cttgctggga ttacttcttc aggttaaccc aacagaaggc tcgagaaggt 2700
atattgctgt tgacagtgag cgagggtgaa gatcctgttc aatatagtga agccacagat 2760
gtatattgaa caggatcttc acccgtgcct actgcctcgg aattcgtgga aaggacgaaa 2820
caccgggggt gaagatcctg ttcaatactc gagtattgaa caggatcttc accctttttg 2880
aattaatggc aactctgaca gatgtggcgg gaggaaagct gaggtgggag tactgctcag 2940
agctacaact ctaggagtag ggactccaag cctagagctc caagagaggg tgaagggcag 3000
ggagaaaatt atagtaatag ttgcaatgag tcacttgctt ctagatcaag atcagagact 3060
ctgctctccg tgttcacagc ggaccttgat ttaatgtcat acaattaagg cacgcggtga 3120
atgccaagag cggagcctac agctgcactt gaaggacatc cgagagaagt taggaagggt 3180
ggggagaaac aattctagaa tgaacccatc ctgtgcgaca caaggacccc tcgcattgat 3240
tcaaaatctt tagaatacaa gacagtcaaa ctgtcggtcc cctctggctc tccgcgtgcg 3300
cccggggctg cgggagcgga gtccgctcag gccccccgcgc cgggtcggcg gcggcacgtg 3360
gggcccacag cgcggcagcg gtgccggcga atgggaggcc cgtttctctc tttggttatc 3420
tagctgtatg agtgccacag agccgtcata aagctagata accgaaagta gaaatgactc 3480
tcacaacttc tgcgtgcgat ggcccggccg gccgccctgg ccacaggagc cagaggagcc 3540
cagagaagcc cacgccaccc agggattcca gctcgacgga gcggccacgc cgggaccagg 3600
tatccgacct cggctctcca attctaaatt tcgaaagtcg acgtcggttg gcgcgccagc 3660
tcgcgccagc tatcaagctc gagtgcttta tttgtgaaat ttgtgatact attgctttat 3720
ttgtaaccat tataagctgc aataaacaag ttaacaacaa caattgcatt cattttattg 3780
tttcaggttc agggggaggt gtgggaggtt ttttaaaggg ggagggggta cgtagataag 3840
tagcatggcg ggttaatcat taactacaag gaacccctag tgatggagtt ggccactccc 3900
tctctgcgcg ctcgctcgct cactgaggcc gggcgaccaa aggtcgcccg acgcccgggc 3960
tttgcccggg cggcctcagt gagcgagcga gcgcgccagc tggcgtaata gcgaagaggc 4020
ccgcaccgat cgcccttccc aacagttgcg cagcctgaat ggcgaatggc gattctgttg 4080
caatggctgg cggtaatatt gttctggata ttaccagcaa ggccgatagt ttgagttctt 4140
ctactcaggc aagtgatgtt attactaatc aaagaagtat tgcgacaacg gttaatttgc 4200
gtgatggaca gactctttta ctcggtggcc tcactgatta taaaaacact tctcaggatt 4260
ctggcgtacc gttcctgtct aaaatccctt taatcggcct cctgtttagc tcccgctctg 4320
attctaacga ggaaagcacg ttatacgtgc tcgtcaaagc aaccatagta cgcgccctgt 4380

-continued

```
agcggcgcat taagcgcggc gggtgtggtg gttacgcgca gcgtgaccgc tacacttgcc   4440
agcgccctag cgcccgctcc tttcgctttc ttcccttcct ttctcgccac gttcgccggc   4500
tttccccgtc aagctctaaa tcgggggctc cctttagggt tccgatttag tgctttacgg   4560
cacctcgacc ccaaaaaact tgattagggt gatggttcac gtagtgggcc atcgccctga   4620
tagacggttt ttcgcccttt gacgttggag tccacgttct ttaatagtgg actcttgttc   4680
caaactggaa caacactcaa ccctatctcg gtctattctt ttgatttata agggattttg   4740
ccgatttcgg cctattggtt aaaaaatgag ctgatttaac aaaaatttaa cgcgaatttt   4800
aacaaaatat taacgtttac aatttaaata tttgcttata caatcttcct gtttttgggg   4860
cttttctgat tatcaaccgg ggtacatatg attgacatgc tagttttacg attaccgttc   4920
atcgattctc ttgtttgctc cagactctca ggcaatgacc tgatagcctt tgtagagacc   4980
tctcaaaaat agctaccctc tccggcatga atttatcagc tagaacggtt gaatatcata   5040
ttgatggtga tttgactgtc tccggccttt ctcacccgtt tgaatcttta cctacacatt   5100
actcaggcat tgcatttaaa atatatgagg gttctaaaaa tttttatcct tgcgttgaaa   5160
taaaggcttc tcccgcaaaa gtattacagg gtcataatgt ttttggtaca accgatttag   5220
ctttatgctc tgaggcttta ttgcttaatt ttgctaattc tttgccttgc ctgtatgatt   5280
tattggatgt tggaatgccc tgatgcggta ttttctcctt acgcatctgt gcggtatttc   5340
acaccgcata tggtgcactc tcagtacaat ctgctctgat gccgcatagt taagccagcc   5400
ccgacacccg ccaacacccg ctgacgcgcc ctgacgggct tgtctgctcc cggcatccgc   5460
ttacagacaa gctgtgaccg tctccgggag ctgcatgtgt cagaggtttt caccgtcatc   5520
accgaaacgc gcgagacgaa agggcctcgt gatacgccta tttttatagg ttaatgtcat   5580
gataataatg gtttcttaga cgtcaggtgg cacttttcgg ggaaatgtgc gcggaacccc   5640
tatttgttta tttttctaaa tacattcaaa tatgtatccg ctcatgagac aataaccctg   5700
ataaatgctt caataatatt gaaaaaggaa gagtatgagt attcaacatt tccgtgtcgc   5760
ccttattccc ttttttgcgg cattttgcct tcctgttttt gctcacccag aaacgctggt   5820
gaaagtaaaa gatgctgaag atcagttggg tgcacgagtg ggttacatcg aactggatct   5880
caacagcggt aagatccttg agagttttcg ccccgaagaa cgttttccaa tgatgagcac   5940
ttttaaagtt ctgctatgtg gcgcggtatt atcccgtatt gacgccgggc aagagcaact   6000
cggtcgccgc atacactatt ctcagaatga cttggttgag tactcaccag tcacagaaaa   6060
gcatcttacg gatggcatga cagtaagaga attatgcagt gctgccataa ccatgagtga   6120
taacactgcg gccaacttac ttctgacaac gatcggagga ccgaaggagc taaccgcttt   6180
tttgcacaac atgggggatc atgtaactcg ccttgatcgt tgggaaccgg agctgaatga   6240
agccatacca aacgacgagc gtgacaccac gatgcctgta gcaatggcaa caacgttgcg   6300
caaactatta actggcgaac tacttactct agcttcccgg caacaattaa tagactggat   6360
ggaggcggat aaagttgcag gaccacttct gcgctcggcc cttccggctg gctggtttat   6420
tgctgataaa tctggagccg gtgagcgtgg gtctcgcggt atcattgcag cactggggcc   6480
agatggtaag ccctcccgta tcgtagttat ctacacgacg gggagtcagg caactatgga   6540
tgaacgaaat agacagatcg ctgagatagg tgcctcactg attaagcatt ggtaactgtc   6600
agaccaagtt tactcatata tactttagat tgatttaaaa cttcattttt aatttaaaag   6660
gatctaggtg aagatccttt ttgataatct catgaccaaa atcccttaac gtgagttttc   6720
gttccactga gcgtcagacc ccgtagaaaa gatcaaagga tcttcttgag atcctttttt   6780
```

tctgcgcgta atctgctgct tgcaaacaaa aaaaccaccg ctaccagcgg tggtttgttt 6840
gccggatcaa gagctaccaa ctctttttcc gaaggtaact ggcttcagca gagcgcagat 6900
accaaatact gtccttctag tgtagccgta gttaggccac cacttcaaga actctgtagc 6960
accgcctaca tacctcgctc tgctaatcct gttaccagtg gctgctgcca gtggcgataa 7020
gtcgtgtctt accgggttgg actcaagacg atagttaccg gataaggcgc agcggtcggg 7080
ctgaacgggg ggttcgtgca cacagcccag cttggagcga acgacctaca ccgaactgag 7140
atacctacag cgtgagctat gagaaagcgc cacgcttccc gaagggagaa aggcggacag 7200
gtatccggta agcggcaggg tcggaacagg agagcgcacg agggagcttc caggggggaaa 7260 cgcctggtat ctttatagtc ctgtcgggtt tcgccacctc tgacttgagc gtcgattttt 7320
gtgatgctcg tcaggggggc ggagcctatg gaaaaacgcc agcaacgcgg cctttttacg 7380
gttcctggcc ttttgctggc cttttgctca catgttcttt cctgcgttat cccctgattc 7440
tgtggataac cgtattaccg cctttgagtg agctgatacc gctcgccgca gccgaacgac 7500
cgagcgcagc gagtcagtga gcgaggaagc ggaagagcgc ccaatacgca aaccgcctct 7560
ccccgcgcgt tggccgattc attaatg 7587

<210> SEQ ID NO 2
<211> LENGTH: 48
<212> TYPE: DNA
<213> ORGANISM: Artificial Sequence
<220> FEATURE:
<223> OTHER INFORMATION: DNA of shRNA to human PTB

<400> SEQUENCE: 2
gcgtgaagat cctgttcaat actcgagtat tgaacaggat cttcacgc 48

<210> SEQ ID NO 3
<211> LENGTH: 48
<212> TYPE: DNA
<213> ORGANISM: Artificial Sequence
<220> FEATURE:
<223> OTHER INFORMATION: DNA of shRNA to mouse PTB

<400> SEQUENCE: 3
gggtgaagat cctgttcaat actcgagtat tgaacaggat cttcaccc 48

<210> SEQ ID NO 4
<211> LENGTH: 89
<212> TYPE: DNA
<213> ORGANISM: Artificial Sequence
<220> FEATURE:
<223> OTHER INFORMATION: DNA encoding human miR-9

<400> SEQUENCE: 4
tggggttatt tttactttcg gttatctagc tttatgaaga ctccacacca ctcatacagc 60
tagataacca aagataacaa ccaaccccg 89

<210> SEQ ID NO 5
<211> LENGTH: 90
<212> TYPE: DNA
<213> ORGANISM: Artificial Sequence
<220> FEATURE:
<223> OTHER INFORMATION: DNA encoding mouse miR-9

<400> SEQUENCE: 5
ggaggcccgt ttctctcttt ggttatctag ctgtatgagt gccacagagc cgtcataaag 60
ctagataacc gaaagtagaa atgactctca 90

<210> SEQ ID NO 6
<211> LENGTH: 59
<212> TYPE: DNA
<213> ORGANISM: Artificial Sequence
<220> FEATURE:
<223> OTHER INFORMATION: DNA encoding mouse miR-124

<400> SEQUENCE: 6
cgtgttcaca gcggaccttg atttaatgtc atacaattaa ggcacgcggt gaatgccaa 59

<210> SEQ ID NO 7
<211> LENGTH: 61
<212> TYPE: DNA
<213> ORGANISM: Artificial Sequence
<220> FEATURE:
<223> OTHER INFORMATION: DNA encoding human miR-124

<400> SEQUENCE: 7
cgtgttcaca gcggaccttg atttaaatgt ccatacaatt aaggcacgcg gtgaatgcca 60
a 61

<210> SEQ ID NO 8
<211> LENGTH: 7575
<212> TYPE: DNA
<213> ORGANISM: Artificial Sequence
<220> FEATURE:
<223> OTHER INFORMATION: Vector AAV-hshPTB-124-9

<400> SEQUENCE: 8
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac gtacatttat 180
attggctcat gtccaacatt accgccatgt tgacattgat tattgactag ttattaatag 240
taatcaatta cggggtcatt agttcatagc ccatatatgg agttccgcgt tacataactt 300
acggtaaatg gcccgcctgg ctgaccgccc aacgaccccc gcccattgac gtcaataatg 360
acgtatgttc ccatagtaac gccaataggg actttccatt gacgtcaatg ggtggagtat 420
ttacggtaaa ctgcccactt ggcagtacat caagtgtatc atatgccaag tacgccccct 480
attgacgtca atgacggtaa atggcccgcc tggcattatg cccagtacat gaccttatgg 540
gactttccta cttggcagta catctacgta ttagtcatcg ctattaccat ggtgatgcgg 600
ttttggcagt acatcaatgg gcgtggatag cggtttgact cacggggatt tccaagtctc 660
caccccattg acgtcaatgg gagtttgttt tggcaccaaa atcaacggga ctttccaaaa 720
tgtcgtaaca actccgcccc attgacgcaa atgggcggta ggcgtgtacg gtgggaggtc 780
tatataagca gagctcgttt agtgaaccgt cagatcgcct ggagacgcca tccacgctgt 840
tttgacctcc atagaagaca ccgggaccga tccagcctcc cctcgaagct ttacatgtgg 900
tacccttcag gtcgacattt atccctaaac aggataacac tagcataact tcgtatagga 960
tactttatac gaagttattc gcgatgaata aatgaaagct tgcagatctg cgactctaga 1020
ggatctgcga ctctagagga tcataatcag ccataccaca ttttgtagag gttttacttg 1080
ctttaaaaaa cctcccacac ctccccctga acctgaaaca taaaatgaat gcaattgttg 1140
ttgttaactt gtttattgca gcttataatg gttacaaata aagcaatagc atcacaaatt 1200
tcacaaataa agcatttttt tcactgcatt ctagttgtgg tttgtccaaa ctcatcaatg 1260

```
tatcttatca tgtctggatc tgcgactcta gaggatcata atcagccata ccacatttgt   1320

agaggtttta cttgctttaa aaaacctccc acacctcccc ctgaacctga aacataaaat   1380

gaatgcaatt gttgttgtta acttgtttat tgcagcttat aatggttaca aataaagcaa   1440

tagcatcaca aatttcacaa ataaagcatt tttttcactg cattctagtt gtggtttgtc   1500

caaactcatc aatgtatctt atcatgtctg gatctgcgac tctagaggat cataatcagc   1560

cataccacat ttgtagaggt tttacttgct ttaaaaaacc tcccacacct cccccctgaac   1620

ctgaaacata aaatgaatgc aattgttgtt gttaacttgt ttattgcagc ttataatggt   1680

tacaaataaa gcaatagcat cacaaatttc acaaataaag catttttttc actgcattct   1740

agttgtggtt tgtccaaact catcaatgta tcttatcatg tctggatccc catcaagctg   1800

atccggaacc cttaatataa cttcgtatag gatactttat acgaagttat tagctagtta   1860

cagtaccggc ttagttagga attgccacca tgagcgagct gatcaaggag aacatgcaca   1920

tgaagctgta catggagggc accgtgaaca accaccactt caagtgcaca tccgagggcg   1980

aaggcaagcc ctacgagggc acccagacca tgaagatcaa ggtggtcgag ggcggccctc   2040

tcccc ttcgc cttcgacatc ctggctacca gcttcatgta cggcagcaaa gccttcatca   2100

accacaccca gggcatcccc gacttcttta agcagtcctt ccctgagggc ttcacatggg   2160

agagaatcac cacatacgaa gacgggggcg tgctgaccgc tacccaggac accagcttcc   2220

agaacggctg catcatctac aacgtcaaga tcaacggggt gaacttccca tccaacggcc   2280

ctgtgatgca gaagaaaaca cgcggctggg aggccaacac cgagatgctg taccccgctg   2340

acggcggcct gagaggccac agccagatgg ccctgaagct cgtgggcggg ggctacctgc   2400

actgctcctt caagaccaca tacagatcca agaaacccgc taagaacctc aagatgcccg   2460

gcttccactt cgtggaccac agactggaaa gaatcaagga ggccgacaaa gagacctacg   2520

tcgagcagca cgagatggct gtggccaagt actgcgacct ccctagcaaa ctggggcaca   2580

gataatcgat agtttgtttg aatgaggctt cagtacttta cagaatcgtt gcctgcacat   2640

cttggaaaca cttgctggga ttacttcttc aggttaaccc aacagaaggc tcgagaaggt   2700

atattgctgt tgacagtgag cgagcgtgaa gatcctgttc aatactcgag tattgaacag   2760

gatcttcacg cgtgcctact gcctcggaat tcgtggaaag gacgaaacac cgggcgtgaa   2820

gatcctgttc aatactcgag tattgaacag gatcttcacg ctttttgaat taatggcaac   2880

tctgacagat gtggcgggag gaaagctgag gtgggagtac tgctcagagc tacaactcta   2940

ggagtaggga ctccaagcct agagctccaa gagagggtga agggcaggga gaaaattata   3000

gtaatagttg caatgagtca cttgcttcta gatcaagatc agagactctg ctctccgtgt   3060

tcacagcgga ccttgattta aatgtccata caattaaggc acgcggtgaa tgccaagagc   3120

ggagcctaca gctgcacttg aaggacatcc gagagaagtt aggaagggtg gggagaaaca   3180

attctagaat gaacccatcc tgtgcgacac aaggacccct cgcattgatt caaaatcttt   3240

agaatacaag acagtcaaac tgtcggtccc ctctggctct ccgcgtgcgc ccggggctgc   3300

gggagcggag tccgctcagg cccccgcgcc gggtcggcgg cggcacgtgg ggcccacagc   3360

gcggcagcgg tgccggcgaa tgtggggtta tttttacttt cggttatcta gctttatgaa   3420

gactccacac cactcataca gctagataac caaagataac aaccaacccc gcaacttctg   3480

cgtgcgatgg cccggccggc cgccctggcc acaggagcca gaggagccca gagaagccca   3540

cgccacccag ggattccagc tcgacggagc ggccacgccg ggaccaggta tccgacctcg   3600
```

-continued

```
gctctccaat tctaaatttc gaaagtcgac gtcggttggc gcgccagctc gcgccagcta   3660
tcaagctcga gtgctttatt tgtgaaattt gtgatactat tgctttattt gtaaccatta   3720
taagctgcaa taaacaagtt aacaacaaca attgcattca ttttattgtt tcaggttcag   3780
ggggaggtgt gggaggtttt ttaaaggggg agggggtacg tagataagta gcatggcggg   3840
ttaatcatta actacaagga acccctagtg atggagttgg ccactccctc tctgcgcgct   3900
cgctcgctca ctgaggccgg gcgaccaaag gtcgcccgac gcccgggctt tgcccgggcg   3960
gcctcagtga gcgagcgagc gcgccagctg gcgtaatagc gaagaggccc gcaccgatcg   4020
cccttcccaa cagttgcgca gcctgaatgg cgaatggcga ttctgttgca atggctggcg   4080
gtaatattgt tctggatatt accagcaagg ccgatagttt gagttcttct actcaggcaa   4140
gtgatgttat tactaatcaa agaagtattg cgacaacggt taatttgcgt gatggacaga   4200
ctcttttact cggtggcctc actgattata aaaacacttc tcaggattct ggcgtaccgt   4260
tcctgtctaa aatcccttta atcggcctcc tgtttagctc ccgctctgat tctaacgagg   4320
aaagcacgtt atacgtgctc gtcaaagcaa ccatagtacg cgccctgtag cggcgcatta   4380
agcgcggcgg gtgtggtggt tacgcgcagc gtgaccgcta cacttgccag cgccctagcg   4440
cccgctcctt tcgctttctt cccttccttt ctcgccacgt tcgccggctt tccccgtcaa   4500
gctctaaatc gggggctccc tttagggttc cgatttagtg ctttacggca cctcgacccc   4560
aaaaaacttg attagggtga tggttcacgt agtgggccat cgccctgata gacggttttt   4620
cgccctttga cgttggagtc cacgttcttt aatagtggac tcttgttcca aactggaaca   4680
acactcaacc ctatctcggt ctattctttt gatttataag ggattttgcc gatttcggcc   4740
tattggttaa aaaatgagct gatttaacaa aaatttaacg cgaattttaa caaaatatta   4800
acgtttacaa tttaaatatt tgcttataca atcttcctgt ttttggggct tttctgatta   4860
tcaaccgggg tacatatgat tgacatgcta gttttacgat taccgttcat cgattctctt   4920
gtttgctcca gactctcagg caatgacctg atagcctttg tagagacctc tcaaaaatag   4980
ctaccctctc cggcatgaat ttatcagcta gaacggttga atatcatatt gatggtgatt   5040
tgactgtctc cggcctttct cacccgtttg aatctttacc tacacattac tcaggcattg   5100
catttaaaat atatgagggt tctaaaaatt tttatccttg cgttgaaata aaggcttctc   5160
ccgcaaaagt attacagggt cataatgttt ttggtacaac cgatttagct ttatgctctg   5220
aggctttatt gcttaatttt gctaattctt tgccttgcct gtatgattta ttggatgttg   5280
gaatgccctg atgcggtatt ttctccttac gcatctgtgc ggtatttcac accgcatatg   5340
gtgcactctc agtacaatct gctctgatgc cgcatagtta agccagcccc gacacccgcc   5400
aacacccgct gacgcgccct gacgggcttg tctgctcccg gcatccgctt acagacaagc   5460
tgtgaccgtc tccgggagct gcatgtgtca gaggttttca ccgtcatcac cgaaacgcgc   5520
gagacgaaag ggcctcgtga tacgcctatt tttataggtt aatgtcatga taataatggt   5580
ttcttagacg tcaggtggca cttttcgggg aaatgtgcgc ggaaccccta tttgtttatt   5640
tttctaaata cattcaaata tgtatccgct catgagacaa taaccctgat aaatgcttca   5700
ataatattga aaaaggaaga gtatgagtat tcaacatttc cgtgtcgccc ttattccctt   5760
ttttgcggca ttttgccttc ctgtttttgc tcacccagaa acgctggtga aagtaaaaga   5820
tgctgaagat cagttgggtg cacgagtggg ttacatcgaa ctggatctca acagcggtaa   5880
gatccttgag agttttcgcc ccgaagaacg ttttccaatg atgagcactt ttaaagttct   5940
gctatgtggc gcggtattat cccgtattga cgccgggcaa gagcaactcg gtcgccgcat   6000
```

-continued

```
acactattct cagaatgact tggttgagta ctcaccagtc acagaaaagc atcttacgga   6060
tggcatgaca gtaagagaat tatgcagtgc tgccataacc atgagtgata acactgcggc   6120
caacttactt ctgacaacga tcggaggacc gaaggagcta accgcttttt tgcacaacat   6180
gggggatcat gtaactcgcc ttgatcgttg ggaaccggag ctgaatgaag ccataccaaa   6240
cgacgagcgt gacaccacga tgcctgtagc aatggcaaca acgttgcgca aactattaac   6300
tggcgaacta cttactctag cttcccggca acaattaata gactggatgg aggcggataa   6360
agttgcagga ccacttctgc gctcggccct tccggctggc tggtttattg ctgataaatc   6420
tggagccggt gagcgtgggt ctcgcggtat cattgcagca ctggggccag atggtaagcc   6480
ctcccgtatc gtagttatct acacgacggg gagtcaggca actatggatg aacgaaatag   6540
acagatcgct gagataggtg cctcactgat taagcattgg taactgtcag accaagttta   6600
ctcatatata ctttagattg atttaaaact tcatttttaa tttaaaagga tctaggtgaa   6660
gatccttttt gataatctca tgaccaaaat cccttaacgt gagttttcgt tccactgagc   6720
gtcagacccc gtagaaaaga tcaaaggatc ttcttgagat cctttttttc tgcgcgtaat   6780
ctgctgcttg caaacaaaaa aaccaccgct accagcggtg gtttgtttgc cggatcaaga   6840
gctaccaact ctttttccga aggtaactgg cttcagcaga gcgcagatac caaatactgt   6900
ccttctagtg tagccgtagt taggccacca cttcaagaac tctgtagcac cgcctacata   6960
cctcgctctg ctaatcctgt taccagtggc tgctgccagt ggcgataagt cgtgtcttac   7020
cgggttggac tcaagacgat agttaccgga taaggcgcag cggtcgggct gaacgggggg   7080
ttcgtgcaca cagcccagct tggagcgaac gacctacacc gaactgagat acctacagcg   7140
tgagctatga gaaagcgcca cgcttcccga agggagaaag gcggacaggt atccggtaag   7200
cggcagggtc ggaacaggag agcgcacgag ggagcttcca gggggaaacg cctggtatct   7260
ttatagtcct gtcgggtttc gccacctctg acttgagcgt cgatttttgt gatgctcgtc   7320
aggggggcgg agcctatgga aaaacgccag caacgcggcc tttttacggt tcctggcctt   7380
ttgctggcct tttgctcaca tgttctttcc tgcgttatcc cctgattctg tggataaccg   7440
tattaccgcc tttgagtgag ctgataccgc tcgccgcagc cgaacgaccg agcgcagcga   7500
gtcagtgagc gaggaagcgg aagagcgccc aatacgcaaa ccgcctctcc ccgcgcgttg   7560
gccgattcat taatg                                                    7575
```

COMPOSITIONS AND METHODS FOR REPROGRAMMING AGE-RESTRICTED NON-NEURONAL CELLS

CROSS REFERENCE TO RELATED APPLICATIONS

This application is a U.S. National Phase application filed under 35 U.S.C. § 371 and claims priority to International Application No. PCT/US2020/054940, filed Oct. 9, 2020, which application claims priority under 35 U.S.C. § 119 to U.S. Provisional Application No. 62/913,104, filed Oct. 9, 2019, the disclosures of which are incorporated herein by reference.

TECHNICAL FIELD

The disclosure relates to methods and composition for differentiating non-neuronal cells to neuronal cells and methods of treating neurodegenerative diseases and disorders.

INCORPORATION BY REFERENCE OF SEQUENCE LISTING

Accompanying this filing is a Sequence Listing entitled, "Sequence-Listing_ST25.txt" created on Oct. 9, 2020 and having 21,814 bytes of data, machine formatted on IBM-PC, MS-Windows operating system. The sequence listing is hereby incorporated by reference in its entirety for all purposes.

BACKGROUND

Regenerative medicine has significant promise for addressing disorders of cell loss or degeneration. The primary approach for regenerative medicine strategies involves cell replacement by introducing pluripotent cells into a subject in order to treat a disease or disorder. This strategy has enjoyed produced successes in treating hematopoietic disorders but has demonstrated limited efficacy in neurodegenerative disorders and disease models. In contrast, strategies aimed at trans-differentiation can take advantage of the existing cellular plasticity of endogenous cells to generate new cell types.

SUMMARY

This disclosure relates to regenerative medicine for neurological diseases and therapeutic compositions and methods for transdifferentiating age-restricted cells to treat neurological degeneration, e.g., age-related neurodegenerative disorders, or neurological damage in elderly subjects.

Provided herein are compositions for generating a functional neuron in vivo comprising: a PTB inhibition agent that suppresses PTB expression or activity; and a miR-9 agent that increases miR-9 expression or activity. In some embodiments the methods and compositions further include a miR-124. In some embodiments, the PTB inhibition agent and the miR-9 agent and the optional miR-124 each comprise an inhibitory nucleic acid molecule. In some embodiments, the inhibitory nucleic acid molecule is a ribonucleic acid polynucleotide. In some embodiments, the PTB inhibition agent and the miR-9 agent and the optional miR-124 are encoded by an expression vector. In some embodiments, the expression vector is a viral vector. In some embodiments, the viral vector is an AAV vector. In some embodiment, the vector comprises a PTB inhibitory agent. In some embodiments, the vector comprises more than one PTB inhibitory agent. In some embodiments, the PTB inhibition agent reduces or inhibits an activity of a PTB polypeptide. In some embodiments, the PTB inhibition agent reduces an amount of a PTB polypeptide within a non-neuronal cell. In some embodiments, the PTB inhibition agent is an anti-PTB inhibitor. In some embodiments, the anti-PTB inhibitor is an antisense oligonucleotide. In some embodiments, the anti-PTB inhibitor is selected from the group consisting of an anti-PTB shRNA, an anti-PTB antisense oligonucleotide, an anti-PTB antibody or fragment thereof, an anti-PTB nanobody, an anti-PTB affibody, an anti-PTB polypeptide, an anti-PTB small molecule, a dominant negative PTB mutant, and a sponge polyribonucleotide containing polypyrimidine. In some embodiments, the PTB inhibitor agent comprises an shPTB agent having a sequence of SEQ ID NO:2 or 3. In some embodiments, a vector of the disclosure comprises 1, 2 or 3 shPTB sequences. In some embodiments, the miR-9 agent increases an amount of a nucleic acid encoding a miR-9 molecule. In some embodiments, the miR-9 agent is a miR-9 ribonucleic acid molecule. In some embodiments, the miR-9 agent inhibits the expression or activity of an nPTB molecule. In some embodiments, the miR-9 agent is an anti-nPTB inhibitor. In some embodiments, the anti-nPTB inhibitor is selected from the group consisting of an anti-nPTB shRNA, an anti-nPTB antisense oligonucleotide, an anti-nPTB antibody or fragment thereof, an anti-nPTB nanobody, an anti-nPTB affibody, an anti-nPTB polypeptide, an anti-nPTB small molecule, a dominant negative nPTB mutant, and a sponge polyribonucleotide containing polypyrimidine. In some embodiment, the a miR-9 agent has a sequence of SEQ ID NO:1 from nucleotide 3409-3469. In some embodiments, the viral vector comprises the PTB inhibition agent of SEQ ID NO:2 or 3 (shPTB), a miR-124 agent (SEQ ID NO:1 from nucleotide 3069-3127, SEQ ID NO:6 or 7) and a miR-9 agent (SEQ ID NO:1 from nucleotide 3409-3469, SEQ ID NO:4 or 5). In a specific embodiment, the vector comprises a sequence that is at least 85%, 90%, 92%, 95%, 97%, 98%, 99% or 100% (or any value between any two of the foregoing values) identical to SEQ ID NO:1.

Also provided in some embodiments are methods of reprogramming a non-neuronal cell into a neuron, the method comprising contacting a composition comprising: a PTB inhibition agent that suppresses PTB expression or activity and a miR-9 agent that increases miR-9 expression or activity and an optional miR-124 with the non-neuronal cell, thereby reprogramming the non-neuronal cell into the neuron. In some embodiments, the non-neuronal cell is a glial cell that expresses miR-9 at a reduced level as compared to a non-neuronal cell from the same brain region of a younger subject. In some embodiments, the glial cell is selected from the group consisting of an astrocyte, an oligodendrocyte, an ependymal cell, a Schwan cell, a NG2 cell, and a satellite cell. In some embodiments, the non-neuronal cell and the neuron are located within a brain of a subject. In some embodiments, the subject has a neurodegenerative disorder. In some embodiments, the neurodegenerative disorder is an age-related neurodegenerative disorder. In some embodiments, the age-related neurodegenerative disorder is selected from the group consisting of Alzheimer's disease, Parkinson's Disease, dementia, stroke, and a disease associated with a loss of functional neurons within the brain of a subject. In some embodiments, the subject is 30 years or older, 40 years or older, 50 years or older, 55 years or older, 60 years or older, 65 years or older, 70 years or older, 75 years or older, or 80 years or older.

Also provided herein are methods of reprogramming a non-neuronal cell into a neuron, the method comprising: contacting the non-neuronal cell with a PTB inhibition agent that suppresses PTB expression or activity and a miR-9 agent that increases miR-9 expression or activity and an optional miR-124 in the non-neuronal cell, thereby reprogramming the non-neuronal cell into the neuron. In some embodiments, the non-neuronal cell is a glial cell that expresses miR-9 at a reduced level as compared to a non-neuronal cell from the same brain region of a younger subject. In some embodiments, the glial cell is selected from the group consisting of an astrocyte, an oligodendrocyte, an ependymal cell, a Schwan cell, a NG2 cell, and a satellite cell. In some embodiments, the PTB inhibition agent reduces or inhibits an expression level of a nucleic acid encoding a PTB polypeptide. In some embodiments, the PTB inhibition agent reduces or inhibits an activity of a PTB polypeptide. In some embodiments, the PTB inhibition agent reduces an amount of a PTB polypeptide within the non-neuronal cell. In some embodiments, the PTB inhibition agent is an anti-PTB inhibitor. In some embodiments, the anti-PTB inhibitor is an antisense oligonucleotide. In some embodiments, the anti-PTB inhibitor is selected from the group consisting of an anti-PTB shRNA, an anti-PTB miRNA, an anti-PTB antisense oligonucleotide, an anti-PTB antibody or fragment thereof, an anti-PTB nanobody, an anti-PTB affibody, an anti-PTB polypeptide, an anti-PTB small molecule, a dominant negative PTB mutant, and a sponge polyribonucleotide containing polypyrimidine. In some embodiments, the miR-9 agent increases an amount of a nucleic acid encoding for a miR-9 molecule. In some embodiments, the miR-9 agent is a miR-9 ribonucleic acid molecule. In some embodiments, the miR-9 agent inhibits the expression or activity of an nPTB molecule. In some embodiments, the miR-9 agent is an anti-nPTB inhibitor. In some embodiments, the anti-nPTB inhibitor is selected from the group consisting of an anti-nPTB shRNA, an anti-nPTB miRNA, an anti-nPTB antisense oligonucleotide, an anti-nPTB antibody or fragment thereof, an anti-nPTB nanobody, an anti-nPTB affibody, an anti-nPTB polypeptide, an anti-nPTB small molecule, a dominant negative nPTB mutant, and a sponge polyribonucleotide containing polypyrimidine. In some embodiments, the PTB inhibition agent suppresses the level of PTB expression or activity for at least 12 hours, at least 24 hours, at least 2 days, at least 3 days, at least 4 days, at least 5 days, at least 10 days, or at least 15 days In some embodiments, the miR-9 agent increases the level of miR-9 expression or activity for at least 12 hours, at least 24 hours, at least 2 days, at least 3 days, at least 4 days, at least 5 days, at least 10 days, or at least 15 days. In some embodiments, the non-neuron cell is located within a brain region. In some embodiments, the neuron is a dopaminergic neuron. In some embodiments, the neuron is a cholinergic neuron.

The disclosure also provides methods of generating a neuron within a subject, the method comprising: administering to a brain region comprising a non-neuronal cell that expresses miR-9 at a reduced level as compared to a young non-neuronal cell of the subject a PTB inhibition agent that suppresses PTB expression or activity and a miR-9 agent that increases miR-9 expression or activity in the non-neuronal cell, thereby reprogramming the non-neuronal cell into the neuron. In some embodiments, the method can further comprise delivery a miR-124 to the non-neuronal cell. In some embodiments, the non-neuronal cell is a glial cell. In some embodiments, the glial cell is selected from the group consisting of an astrocyte, an oligodendrocyte, an ependymal cell, a Schwan cell, and a satellite cell. In some embodiments, the PTB inhibition agent reduces or inhibits an expression level of a nucleic acid encoding a PTB polypeptide. In some embodiments, the PTB inhibition agent reduces or inhibits an activity of a PTB polypeptide. In some embodiments, the PTB inhibition agent reduces an amount of a PTB polypeptide within the non-neuronal cell. In some embodiments, the PTB inhibition agent is an anti-PTB inhibitor. In some embodiments, the anti-PTB inhibitor is an antisense oligonucleotide. In some embodiments, the anti-PTB inhibitor is selected from the group consisting of an anti-PTB shRNA, an anti-PTB miRNA, an anti-PTB antisense oligonucleotide, an anti-PTB antibody or fragment thereof, an anti-PTB nanobody, an anti-PTB affibody, an anti-PTB polypeptide, an anti-PTB small molecule, a dominant negative PTB mutant, and a sponge polyribonucleotide containing polypyrimidine In some embodiments, the miR-9 agent increases an amount of a nucleic acid encoding for a miR-9 molecule. In some embodiments, the miR-9 agent is a miR-9 ribonucleic acid molecule. In some embodiments, the miR-9 agent inhibits the expression or activity of an nPTB molecule. In some embodiments, the miR-9 agent is an anti-nPTB inhibitor. In some embodiments, the anti-nPTB inhibitor is selected from the group consisting of an anti-nPTB shRNA, an anti-nPTB miRNA, an anti-nPTB antisense oligonucleotide, an anti-nPTB antibody or fragment thereof, an anti-nPTB nanobody, an anti-nPTB affibody, an anti-nPTB polypeptide, an anti-nPTB small molecule, a dominant negative nPTB mutant, and a sponge polyribonucleotide containing polypyrimidine. In some embodiments, the functional neuron is a dopaminergic neuron In some embodiments, the functional neuron is a cholinergic neuron. In some embodiments, the administering of the PTB inhibition agent and the miR-9 agent comprises administering a viral vector comprising a nucleic acid encoding the PTB inhibition agent and the miR-9 agent. In some embodiments, the administering the PTB inhibition agent and the miR-9 agent comprises administering a viral vector comprising a nucleic acid encoding the PTB inhibition agent and a viral vector comprising a nucleic acid encoding the miR-9 agent. In some embodiments, the administering comprises contacting a non-neuronal cell with the PTB inhibition agent and the miR-9 agent. In some embodiments, the subject comprises a phenotype wherein contacting the non-neuronal cell within the brain of the subject with the PTB inhibition agent alone does not reprogram the non-neuronal cell into a functional neuron. In some embodiments, the subject is an elderly individual with a brain injury or an individual with an age-related neurodegenerative disorder. In some embodiments, the age-related neurodegenerative disorder is selected from the group consisting of Alzheimer's Disease, Parkinson's Disease, dementia, stroke, and a disease associated with a loss of functional neurons within the brain of a subject.

The disclosure also provides methods of treating a neurological condition associated with the degeneration of functional neurons within a brain of a subject, the method comprising: contacting a non-neuronal cell with a PTB inhibition agent that suppresses PTB expression or activity and a miR-9 agent that increases miR-9 expression or activity in the non-neuronal cell, thereby reprogramming the non-neuronal cell into the neuron and treating the neurological condition. In some embodiments, the contacting with the PTB inhibition agent and the miR-9 agent is performed simultaneously. In some embodiments, the contacting comprises co-administering the PTB inhibition agent and the miR-9 agent to a region of the brain comprising the non-neuronal cell of the subject. In some embodiments, the co-administering the PTB inhibition agent and the miR-9 agent comprises administering a single viral vector comprising a nucleic acid encoding the PTB inhibition agent and the miR-9 agent. In some embodiments, the neurological disorder is a neurodegenerative disorder. In some embodiments, the neurodegenerative disorder is an age-related neurodegenerative disorder. In some embodiments, the subject comprises a phenotype wherein contacting the non-neuronal cell within the brain of the subject with the PTB inhibition agent alone does not reprogram the non-neuronal cell into a functional neuron. In some embodiments, the non-neuronal cell is a glial cell. In some embodiments, the glial cell is selected from the group consisting of an astrocyte, an oligodendrocyte, an ependymal cell, a Schwan cell, a NG2 cell, and a satellite cell.

The disclosure also provides methods of generating a neuron within a brain of a subject, the method comprising: contacting a non-neuronal cell that is located within a region of the brain that the functional neuron originates from with a PTB inhibition agent that suppresses PTB expression or activity, thereby reprogramming the non-neuronal cell into the neuron. In some embodiments, the method further comprises: contacting a non-neuronal cell that is located within a region of the brain that the functional neuron originates with a miR-9 agent that increases miR-9 expression or activity in the non-neuronal cell and optionally a miR-124. In some embodiments, the functional neuron is a dopaminergic neuron and the non-neuronal cell that is located within a mesencephalon region of the brain. In some embodiments, the functional neuron is a cholinergic neuron and the non-neuronal cell that is located within a basal forebrain region of the brain. In some embodiments, the functional neuron comprises a transcriptional phenotype similar to the non-neuronal cell that is located within a region of the brain. In some embodiments, the non-neuronal cell is a glial cell. In some embodiments, the non-neuronal cell is an astrocyte.

The disclosure provides methods of generating a functional neuron within a brain of a subject with Alzheimer's Disease, the method comprising: contacting a non-neuronal cell with a PTB inhibition agent that suppresses PTB expression or activity and a miR-9 agent that increases miR-9 expression or activity, thereby reprogramming the non-neuronal cell into a functional neuron, wherein the non-neuronal cell is within a region of the brain from which the functional neuron originates.

The disclosure also provides methods of generating a functional neuron within a brain of a subject with Parkinson's Disease, the method comprising: contacting a non-neuronal cell with a PTB inhibition agent that suppresses PTB expression or activity and a miR-9 agent that increases miR-9 expression or activity, thereby reprogramming the non-neuronal cell into a functional neuron wherein the non-neuronal cell is within a region of the brain from which the functional neuron originates.

The disclosure provides kits for generating a functional neuron within a brain of a subject comprising: a PTB inhibition agent that suppresses PTB expression or activity; a miR-9 agent that increases miR-9 expression or activity; and a set of instructions for administering the PTB inhibition agent and the miR-9 agent to the brain of the subject.

BRIEF DESCRIPTION OF THE DRAWINGS

An understanding of the features and advantages of the invention will be obtained by reference to the following detailed description that sets forth illustrative embodiments, in which the principles of the invention are utilized, and the accompanying drawings of which:

FIG. 2B shows quantitation of cell survival (left) and converted Tuj1-positive neurons (right) in response to shPTB treatment alone or in combination with miR-9 overexpression. FIG. 2C shows western blotting analysis of Tau and Tuj1 expression in response to shPTB treatment alone or in combination with miR-9 overexpression. FIG. 2D shows the expression of the constructs of FIG. 2E measured by RT-PCR. FIG. 2E provides exemplary constructs of the disclosure.

FIG. 7 provides an exemplary sequence of a construct of the disclosure (SEQ ID NO:1) annotated to show various domain/coding sequences. SEQ ID NO:8 is similar containing human sequences.

DETAILED DESCRIPTION

Figure 1:
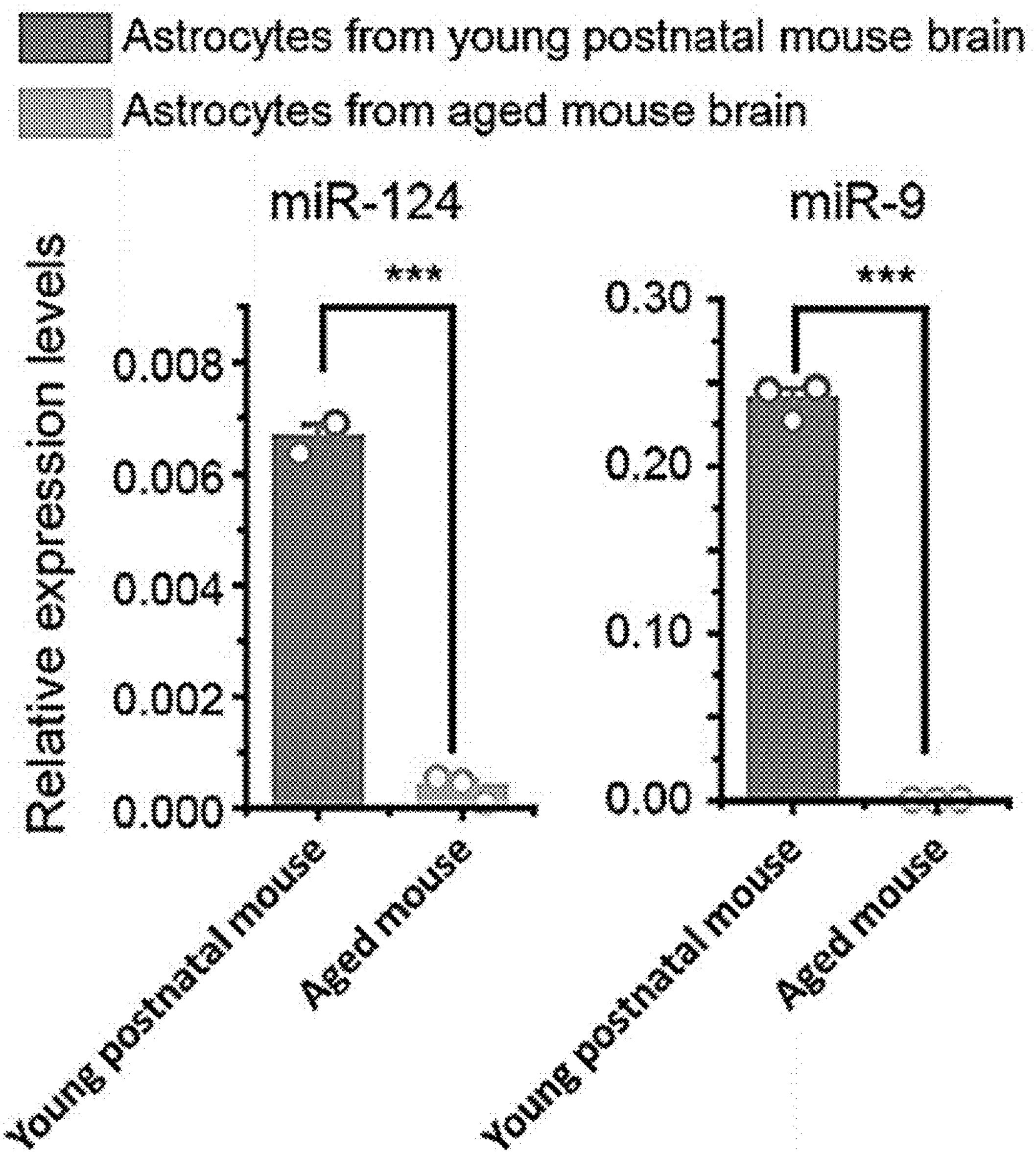
FIG. 1 shows exemplary data from quantitative PCR analysis of key microRNAs in astrocytes derived from mice of different ages. Young astrocytes were isolated from the brain of postnatal day 5 mice. Old astrocytes were isolated from the brain of postnatal day 180 mice. miR-124 and miR-9 expression levels are shown.

As used herein and in the appended claims, the singular forms "a," "an," and "the" include plural referents unless the context clearly dictates otherwise. Thus, for example, reference to "a sample" includes a plurality of such samples and reference to "the cell" includes reference to one or more cells, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Throughout this application, the term "about" is used to indicate that a value that can include similar values or that a value can include the standard deviation of error for the device or method being employed to determine the value. The term "about" when used before a numerical designation, e.g., temperature, time, amount, and concentration, including range, indicates approximations which may vary by (+) or (−) 20%, 10%, 5%, or 1%.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

"Age" can refer to the age of a subject or the age of cell within the subject. Non-limiting examples of age-related neurodegenerative disorders include Alzheimer's disease, Parkinson's disease, dementia, Huntington's disease, Downs syndrome (DS), DS-linked early onset of Alzheimer's (DS-AD), stroke, and Amyotrophic lateral sclerosis. In some embodiments, the age-related neurodegenerative disorders is Alzheimer's disease, Parkinson's disease, dementia, or Huntington's disease. In some embodiments, the age-related neurodegenerative disorders is Alzheimer's disease. In some embodiments, the age-related neurodegenerative disorders is Parkinson's disease. In some embodiments, the age-related neurodegenerative disorders is dementia. In some embodiments, the age-related neurodegenerative disorders is Huntington's disease. In some embodiments, the age-related neurodegenerative disorders is amyotrophic lateral sclerosis. In some embodiments, the age-related neurodegenerative disorders is DS-AD.

"Astrocyte" can refer to characteristic star-shaped glial cells in the brain and spinal cord. As would be clear to one skilled in the art, astrocytes can be characterized in their star shape, expression of markers like glial fibrillary acidic protein (GFAP) and aldehyde dehydrogenase 1 family member L1 (ALDH1L1), excitatory amino acid transporter 1/glutamate aspartate transporter (EAAT1/GLAST), glutamine synthetase, S100 beta, or excitatory amino acid transporter 1/glutamate transporter 1 (EAAT2/GLT-1), participation of blood-brain barrier together with endothelial cells, transmitter uptake and release, regulation of ionic concentration in extracellular space, reaction to neuronal injury and participation in nervous system repair, and metabolic support of surrounding neurons. In certain cases of the present disclosure, an astrocyte can refer to a non-neuronal cell in a nervous system that expresses glial fibrillary acidic protein (GFAP), Aldehyde Dehydrogenase 1 Family Member L1 (ALDH1L1), or both. In certain cases, an astrocyte can refer to a nonneuronal cell in a nervous system that expresses a glial fibrillary acidic protein (GFAP) promoter-driven transgene (e.g., red fluorescent protein (RFP), Cre recombinase).

"Cell lineage" or "lineage" can denote the developmental history of a tissue or organ from the fertilized embryo.

As used herein, the term "contacting" cells with a composition of the disclosure refers to placing the composition (e.g., compound, nucleic acid, viral vector etc.) in a location that will allow it to touch the cell in order to produce "contacted" cells. The contacting may be accomplished using any suitable method. For example, in one embodiment, contacting is by adding the compound to a culture of cells. Contacting may also be accomplished by injecting it or delivering the composition to a location within a body such that the composition "contacts" the cell type targeted.

"Detecting the presence of" can include determining the amount of something present in addition to determining whether it is present or absent depending on the context.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative, or quantitative and qualitative determinations. Assessing can be relative or absolute.

As used herein, the term "differentiation", of "differentiate" or "converting" of "inducing differentiation" are used interchangeably to refer to changing the default cell type (genotype and/or phenotype) to a non-default cell type (genotype and/or phenotype). Thus "inducing differentiation in an astrocyte cell" refers to inducing the cell to change its morphology from an astrocyte to a neuronal cell type (i.e., change in gene expression as determined by genetic analysis such as a microarray) and/or phenotype (i.e. change in expression of a protein).

The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay.

As used herein, the term "functional neuron" can refer to a neuron that is able to send or receive information through chemical or electrical signals. In some cases, a functional neuron exhibits one or more functional properties of a mature neuron that exists in a normal nervous system, including, but not limited to: excitability (e.g., ability to exhibit action potential, e.g., a rapid rise and subsequent fall in voltage or membrane potential across a cellular membrane), forming synaptic connections with other neurons, presynaptic neurotransmitter release, and post-synaptic response (e.g., excitatory postsynaptic current or inhibitory postsynaptic current). In some cases, a functional neuron is characterized in its expression of one or more markers of functional neurons, including, but not limited to, synapsin, synaptophysin, glutamate decarboxylase 67 (GAD67), glutamate decarboxylase 67 (GAD65), parvalbumin, dopamine- and cAMP-regulated neuronal phosphoprotein 32 (DARPP32), vesicular glutamate transporter 1 (vGLUT1), vesicular glutamate transporter 2 (vGLUT2), acetylcholine, tyrosine hydroxylase (TH), dopamine, vesicular GABA transporter (VGAT), and gamma-aminobutyric acid (GABA).

The term "glial cell" can generally refer to a type of supportive cell in the central nervous system (e.g., brain and spinal cord) and the peripheral nervous system. In some cases, unlike neurons, glial cells do not conduct electrical impulses or exhibit action potential. In some cases, glial cells do not transmit information with each other, or with neurons via synaptic connection or electrical signals. In a nervous system or in an in vitro culture system, glial cells can surround neurons and provide support for and insulation between neurons. Non-limiting examples of glial cells include oligodendrocytes, astrocytes, ependymal cells, Schwann cells, and satellite cells.

The term "in vivo" is used to describe an event that takes place in a subject's body.

The terms "iRNA", "RNAi agent," "iRNA agent,", "RNA interference agent" as used interchangeably herein, refer to an agent that contains RNA, and which mediates the targeted cleavage of an RNA transcript via an RNA-induced silencing complex (RISC) pathway. iRNA directs the sequence-specific degradation of mRNA through a process known as RNA interference (RNAi). For example, iRNA can modulate, e.g., inhibits, the expression of PTB in a cell, e.g., a cell within a subject, such as a mammalian subject. RNAi agents include, without limitation, "small interfering RNA (siRNA)", "endoribonuclease-prepared siRNA (e-siRNA)", "short hairpin RNA (shRNA)", and "small temporally regulated RNA (stRNA)"; "diced siRNA (d-siRNA)", and aptamers, oligonucleotides and other synthetic nucleic acids that comprise at least one uracil base. In some embodiments, such RNAi agents are delivered by a vector such as, but not limited to, a replication defective or replication competent viral vector (e.g., adenoviral vectors, lentiviral vectors, gamma-retroviral vectors etc.).

As used herein, the term "mature neuron" can refer to a differentiated neuron. In some cases, a neuron is to be a mature neuron if it expresses one or more markers of mature neurons, e.g., microtubule-associated protein 2 (MAP2) and Neuronal Nuclei (NeuN), neuron specific enolase (NSE), 160 kDa neurofilament medium, 200 kDa neurofilament heavy, postsynaptic density protein 95(PDS-95), Synapsin I, Synaptophysin, glutamate decarboxylase 67 (GAD67), glutamate decarboxylase 67 (GAD65), parvalbumin, dopamine- and cAMP-regulated neuronal phosphoprotein 32 (DARPP32), vesicular glutamate transporter 1 (vGLUT1), vesicular glutamate transporter 2 (vGLUT2), acetylcholine, and/or tyrosine hydroxylase (TH).

A "microRNA" or "miRNA" refers to a non-coding nucleic acid (RNA) sequence that binds to at least partially complementary nucleic acid sequence (mRNAs) and negatively regulates the expression of the target mRNA at the post-transcriptional level. A microRNA is typically processed from a "precursor" miRNA having a double-stranded, hairpin loop structure to a "mature" form. Typically, a mature microRNA sequence is about 19-25 nucleotides in length.

"miR-9" is a short non-coding RNA gene involved in gene regulation and highly conserved from Drosophila and mouse to human. The mature ~21 nt miRNAs are processed from hairpin precursor sequences by the Dicer enzyme. miR-9 can be one of the most highly expressed microRNAs in developing and adult vertebrate brain. Key transcriptional regulators such as FoxG1, Hes1 or Tlx, can be direct targets of miR-9, placing it at the core of the gene network controlling the neuronal progenitor state.

The sequence of miR-9 is reported mirbase.org. See also Yoo, A. S., Staahl, B. T., Chen, L., & Crabtree, G. R., MicroRNA-mediated switching of chromatin-remodeling complexes in neural development. Nature 460 (7255), 642-646 (2009). In one such embodiment, a third microRNA of interest is miR-124.

A miR-9 agent can comprise any agent that mimics or replicates the function of miR-9 within a cell. A miR-9 agent can be any agent that decreases the expression or activity of nPTB. In some cases, the miR-9 agent can be a small chemical molecule, interfering RNA, short hairpin RNA, microRNA, dominant negative PTB, sponge polynucleotide, ribozyme, antisense oligonucleotide, monoclonal antibody, or polyclonal antibody that is configured to suppress the expression or activity of nPTB.

In certain cases the miR-9 agent increases the expression of miR-9 within a cell. In certain cases, the miR-9 agent increases an amount of a nucleic acid encoding a miR-9 molecule. In one embodiment, the miR-9 agent is a miR-9 ribonucleic acid molecule. A miR-9 agent that increases the expression of miR-9 can be an expression plasmid, an expression vector, or an expression cassette containing a gene encoding miR-9. The expression plasmid, vector, or cassette once delivered to a non-neuronal cell can the express miR-9 from a miR-9 gene encoded in the plasmid.

In some embodiments, the miR-9 agent is one that suppresses the expression or activity of nPTB, and can be any type of reagent that suppresses or eliminates the protein expression or protein activity of nPTB. In some cases, the miR-9 agent can be a small chemical molecule, interfering RNA, short hairpin RNA, microRNA, dominant negative nPTB, sponge polynucleotide, ribozyme, antisense oligonucleotide, monoclonal antibody, or polyclonal antibody that is configured to suppress the expression or activity of nPTB. In certain cases, the miR-9 agent inhibits the expression or activity of an nPTB molecule. In certain instances, the anti-nPTB inhibitor comprises an anti-nPTB shRNA, an anti-nPTB antisense oligonucleotide, an anti-nPTB antibody or fragment thereof, an anti-nPTB nanobody, an anti-nPTB affibody, an anti-nPTB polypeptide, an anti-nPTB small molecule, a dominant negative nPTB mutant, a nPTB miRNA, or a sponge polyribonucleotide containing polypyrimidine. In some instances, the composition may only comprise an anti-nPTB agent or miR-9 agent.

In certain instances, the miR-9 agent increases the expression or activity of miR-9 by at least about 2 fold, at least about 4 fold, at least about 6 fold, at least about 8 fold, at least about 10 fold, at least about 20 fold, at least about 50 fold, or at least about 100 fold.

In certain instances, the miR-9 agent suppresses or reduces the expression or activity of nPTB by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the endogenous or native level. In some cases, a miR-9 agent as provided herein directly suppress the expression level of nPTB, e.g., suppressing the transcription, translation, or protein stability of nPTB. In some cases, the miR-9 agent as provided herein directly suppresses the activity of nPTB, e.g., blocking the binding of nPTB to its target molecules. In some cases, the miR-9 agent as provided herein directly effects on the expression or activity of nPTB, without affecting other cellular signaling pathway.

The sequence miR-124 is reported at the website having an address of "mirbase.org" wherein www. is placed before the address. See also Yoo, A. S., Staahl, B. T., Chen, L., & Crabtree, G. R., MicroRNA-mediated switching of chromatin-remodelling complexes in neural development. Nature 460 (7255), 642-646 (2009).

miR-124 can optionally be provided in the same or a separate vector to promote neuronal induction by targeting PTB to reduce its expression. It is thought that when PTB inactivation is experimentally induced by shPTB, such negative REST/miR-124 loop is converted to a positive one to allow miR-124 to be more efficient in targeting REST and reduced REST further de-represses miR-124. Once this loop is activated, cells are progressively converted to functional neurons.

A miR-124 agent can comprise any agent that mimics or replicates the function of miR-124 within a cell. In some cases, the miR-124 agent can be a small chemical molecule, interfering RNA, short hairpin RNA, microRNA, dominant negative PTB, sponge polynucleotide, ribozyme, antisense oligonucleotide, monoclonal antibody, or polyclonal antibody that is configured to regulate PTB expression or activity and/or modulate REST.

The term "neurodegenerative disorder" is used in reference to diseases associated with a loss of functional neurons or an increase of neuronal dysfunction within a subject. Age-related neurodegenerative disorders can be associated and/or caused by the process of aging.

The term "neuron" or "neuronal cell" as used herein can have the ordinary meaning one skilled in the art would appreciate. In some cases, neuron can refer to an electrically excitable cell that can receive, process, and transmit information through electrical signals (e.g., membrane potential discharges) and chemical signals (e.g., synaptic transmission of neurotransmitters). As one skilled in the art would appreciate, the chemical signals (e.g., based on release and recognition of neurotransmitters) transduced between neurons can occur via specialized connections called synapses.

"Neuronal lineage" can refer to the developmental history from a neural stem cell to a mature neuron, including the various stages along this process (as known as neurogenesis), such as, but not limited to, neural stem cells (neuroepithelial cells, radial glial cells), neural progenitors (e.g., intermediate neuronal precursors), neurons, astrocytes, and oligodendrocytes.

The term "non-neuronal cell" can refer to any type of cell that is not a neuron. An exemplary nonneuronal cell is a cell that is of a cellular lineage other than a neuronal lineage (e.g., a hematopoietic lineage). In some embodiments, a non-neuronal cell is a cell of neuronal lineage but not a neuron, for example, a glial cell. In some embodiments, a non-neuronal cell is somatic cell that is not neuron, such as, but not limited to, glial cell, adult primary fibroblast, embryonic fibroblast, epithelial cell, melanocyte, keratinocyte, adipocyte, blood cell, bone marrow stromal cell, Langerhans cell, muscle cell, rectal cell, or chondrocyte. In some embodiments, a non-neuronal cell is from a non-neuronal cell line, such as, but not limited to, glioblastoma cell line, Hela cell line, NT2 cell line, ARPE19 cell line, or N2A cell line.

A "nucleic acid molecule" or "polynucleotide" can be composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The terms "nucleic acid" and "polynucleotide" as used interchangeably herein can refer to deoxyribonucleotides or ribonucleotides and polymers thereof in either single- or double-stranded form. The term can encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, locked nucleic acids (LNAs), and peptide-nucleic acids (PNAs). As used in this disclosure, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be RNA, DNA, analogs thereof, or a combination thereof. A nucleic acid encoding all or part of a RNA molecule, antisense oligonucleotide, polypeptide, vector, viral vector, gene therapy, or other biomolecules may contain a contiguous nucleic acid sequence encoding all or a portion of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs. It is also contemplated that a particular polypeptide from a given species may be encoded by nucleic acids containing natural variations that have slightly different nucleic acid sequences but, nonetheless, encode the same or substantially similar protein, polypeptide, or peptide. Any sequence provided herein includes both RNA ("T" replaced with "U") or DNA sequence ("U" replaced with "T") including full length sequences and fragments (e.g., domains of a polynucleotide).

"Oligodendrocyte" can refer to a type of glial call that can create myelin sheath that surrounds a neuronal axon to provide support and insulation to axons in the central nervous system. Oligodendrocyte can also be characterized in their expression of PDGF receptor alpha (PDGFR-α), SOX10, neural/glial antigen 2 (NG2), Olig 1, 2, and 3, oligodendrocyte specific protein (OSP), Myelin basic protein (MBP), or myelin oligodendrocyte glycoprotein (MOG).

"Pluripotent" can refer to the ability of a cell to form all lineages of the body or soma (i.e., the embryo proper). Exemplary "pluripotent stem cells" can include embryonic stem cells and induced pluripotent stem cells.

"Polypyrimidine tract binding protein" or "PTB" and its homolog neural PTB (nPTB) are both RNA-binding proteins with PTB being expressed ubiquitously in most cell types except neurons whereas nPTB being exclusively expressed in developing neurons. PTB can also be called polypyrimidine tract-binding protein 1, and in humans is encoded by the PTBP1 gene. The PTBP1 gene belongs to the subfamily of ubiquitously expressed heterogeneous nuclear ribonucleoproteins (hnRNPs). The hnRNPs are RNA-binding proteins and they complex with heterogeneous nuclear RNA (hnRNA). These proteins are associated with pre-mRNAs in the nucleus and appear to influence pre-mRNA processing and other aspects of mRNA metabolism and transport. PTB can have four repeats of quasi-RNA recognition motif (RRM) domains that bind RNAs. Consistent with its widespread expression, PTB can contribute to the repression of a large number of alternative splicing events. PTB can recognize short RNA motifs, such as UCUU and UCUCU, located within a pyrimidine-rich context and often associated with the polypyrimidine tract upstream of the 3' splice site of both constitutive and alternative exons. In some cases, binding site for PTB can also include exonic sequences, sequences in introns downstream of regulated exons, and sequences in 3' untranslated regions (3'UTRs). In most alternative splicing systems regulated by PTB, repression can be achieved through the interaction of PTB with multiple PTB binding sites surrounding the alternative exon. In some cases, repression can involve a single PTB binding site. Splicing repression by PTB can occur by a direct competition between PTB and U2AF65, which in turn can preclude the assembly of the U2 snRNP on the branch point. In some cases, splicing repression by PTB can involve PTB binding sites located on both sides of alternative exons, and can result from cooperative interactions between PTB molecules that would loop out the RNA, thereby making the splice sites inaccessible to the splicing machinery. Splicing repression by PTB can also involve multimerization of PTB from a high-affinity binding site that can create a repressive wave that covers the alternative exon and prevents its recognition. PTB can be widely expressed in non-neuronal cells, while nPTB can be restricted to neurons. PTB and nPTB can undergo a programmed switch during neuronal differentiation. During neuronal differentiation, PTB is gradually down-regulated at the neuronal induction stage, coincidentally or consequentially, nPTB level is gradually upregulated to a peak level. Later, when the neuronal differentiation enters into neuronal maturation stage, nPTB level experiences reduction after its initial rise and then returns to a relatively low level as compared to the its peak level during neuronal differentiation, when the cell develops into a mature neuron. The sequences of PTB are known (see e.g., Romanelli et al. (2005) Gene, August 15:356:11-8; Robinson et al., PLoS One. 2008 Mar. 12; 3(3):e1801. doi:10.1371/journal.pone.0001801; Makeyev et al., Mol. Cell (2007) August 3; 27(3):435-48); thus, one of skill in the art can design and construct antisense, miRNA, siRNA molecules and the like to modulate, e.g., to decrease or inhibit, the expression of PTB; to practice the methods of this disclosure.

The term "reprogramming" or "trans-differentiation" can refer to the generation of a cell of a certain lineage (e.g., a neuronal cell) from a different type of cell (e.g., a fibroblast cell) without an intermediate process of dedifferentiating the cell into a cell exhibiting pluripotent stem cell characteristics.

As used herein, "small molecules" can refer to small organic or inorganic molecules of molecular weight below about 3,000 Daltons. The small molecules can be natural products or synthetic products.

The terms "subject," "individual," or "patient" are often used interchangeably herein and refer to, except where indicated, mammals such as humans or non-human primates. In some embodiments, the subject is a human. In some embodiments, the subject is diagnosed with a neurodegenerative disorder. In some embodiments, the subject is suspected of or is at high risk for a disease.

As used herein, the terms "treatment" or "treating" are used in reference to a pharmaceutical composition or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

A "vector" is a nucleic acid that can be capable of transporting another nucleic acid into a cell. A vector can be capable of directing expression of a protein or proteins encoded by one or more genes, or a microRNA encoded by a polynucleotide, carried by the vector when it is present in the appropriate environment. A vector can be a viral vector, plasmid, cosmid etc. and can be an RNA or a DNA vector.

A "viral vector" is a viral-derived nucleic acid that can be capable of transporting another nucleic acid into a cell. A viral vector can be capable of directing expression of a protein or proteins encoded by one or more genes, or a microRNA encoded by a polynucleotide, carried by the vector when it is present in the appropriate environment. In some embodiments, the nucleic acid is encapsidated in a virus. Examples of viral vectors include, but are not limited to, retroviral, adenoviral, lentiviral and adeno-associated viral vectors (AAV). An AAV vector can be an AAV2, AAV8, or AAV9 vector.

In order to develop regenerative neuro-medicine strategies that leverage trans-differentiation for broad therapeutic applications, there are multiple barriers to be overcome. It is well known in the field of neuroscience that astrocytes from older subjects are more difficult to convert than those from young subjects. Even with embryonic astrocytes, it becomes increasingly difficult to convert them after passaging in in vitro cell culture. Such properties can be related to the general problem known as age restriction. In order to develop approaches to treat neurodegenerative diseases in humans, the age restriction barrier needs to be both understood and overcome.

Disclosed herein, are compositions and methods that overcome age restriction for generating functional neurons within a subject and treating neurodegenerative disorders.

Disclosed herein are compositions and methods for reprogramming non-neuronal cells into functional neurons. In some cases, the non-neuronal cells exhibit an age-restricted phenotype. An age-restricted phenotype can comprise any number of phenotypic changes resulting from the process of aging.

Disclosed herein are compositions for generating a functional neuron in vivo that comprise (a) a PTB inhibition agent that suppresses PTB expression or activity; (b) a miR-9 agent that increases miR-9 expression or activity and optionally (c) an miR-124. In certain cases, the functional neuron is generated in a subject.

In certain cases, the PTB inhibition agent reduces or inhibits an activity of a PTB polypeptide. In certain cases, the PTB inhibition agent reduces an amount of a PTB polypeptide within a non-neuronal cell. In certain cases, the PTB inhibition agent is an anti-PTB inhibitor. In certain instances, the anti-PTB inhibitor comprises an antisense oligonucleotide (ASO), an anti-PTB shRNA, an anti-PTB siRNA, an anti-PTB miRNA, an anti-PTB antibody or fragment thereof, an anti-PTB nanobody, an anti-PTB affibody, an anti-PTB polypeptide, an anti-PTB small molecule, a dominant negative PTB mutant, or a sponge polyribonucleotide containing polypyrimidine.

As provided herein, a PTB inhibition agent that suppresses the expression or activity of PTB can be any type of reagent that suppresses or eliminates the protein expression or protein activity of PTB. In some cases, the PTB inhibition agent can be a small chemical molecule, interfering RNA, short hairpin RNA, microRNA, dominant negative PTB, sponge polynucleotide, ribozyme, antisense oligonucleotide, monoclonal antibody, or polyclonal antibody that is configured to suppress the expression or activity of PTB.

A small chemical molecule inhibitor of PTB can be an organic or inorganic chemical compound. The small molecule inhibitor of PTB can have a structure that is based on an active fragment of PTB. For example, computer modeling methods known in the can be used to rationally design a molecule that has a structure similar to an active fragment of PTB, for example, the RNA-binding motifs (e.g., 1, 2, 3, 4, or more different RNA-binding motifs).

RNA interference (RNAi) can be useful for reducing the expression level of target gene PTB. As provided herein, the methods can include use of small hairpin RNA (shRNA) for suppressing expression of PTB in a non-neuronal cell. shRNA molecules are believed to direct sequence-specific degradation of mRNA in cells of various types after first undergoing processing by an RNase III enzyme called DICER (Bernstein et al., Nature 409: 363, 2001) into smaller dsRNA molecules comprised of two 21 nt strands, each of which has a 5' phosphate group and a 3' hydroxyl, and includes a 19 nt region precisely complementary with the other strand, so that there is a 19 nt duplex region flanked by 2 nt-3' overhangs. RNAi can thus be mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides.

A short, interfering RNA (siRNA) that can be use in the methods provided herein can comprise an RNA duplex that can be approximately 19 base pairs long and optionally further comprise one or two single-stranded overhangs or loops, resulting in a total length of between approximately 21 and 23 nucleotides. A siRNA can comprise two RNA strands hybridized together, or can alternatively comprise a single RNA strand that includes a self-hybridizing portion. siRNAs can include one or more free strand ends, which can include phosphate and/or hydroxyl groups. siRNAs typically can include a portion that hybridizes under stringent conditions with a target transcript. One strand of the siRNA (or, the self-hybridizing portion of the siRNA) can be precisely complementary with a region of the target transcript (e.g., PTB mRNA transcript), meaning that the siRNA hybridizes to the target transcript without a single mismatch. In certain cases, perfect complementarity is not achieved. In some cases, the mismatches are located at or near the siRNA termini.

siRNAs can also include various RNA structures (e.g., short hairpin RNAs (shRNAs)) that can be processed in vivo to generate such molecules. shRNAs can include RNA strands containing two complementary elements that hybridize to one another to form a stem, a loop, and optionally an overhang, e.g., a 3' overhang. The stem can be approximately 19 bp long, the loop about 1-20, e.g., about 4-10, and about 6-8 nt long, and/or the overhang about 1-20, e.g., about 2-15 nt long. In certain cases, the stem can be minimally 19 nucleotides in length and can be up to approximately 29 nucleotides in length. Classical siRNAs as provided herein can trigger degradation of mRNAs to which they are targeted (e.g., PTB mRNA transcript), thereby also reducing the rate of protein synthesis. In some cases, certain siRNAs (e.g., microRNAs) that bind to the 3' UTR of PTB mRNA transcript can inhibit expression of a protein encoded by the template transcript by a mechanism related to but distinct from classic RNA interference, e.g., by reducing translation of the transcript rather than decreasing its stability. MicroRNAs can be between approximately 20 and 26 nucleotides in length, e.g., 22 nt in length. MicroRNAs can be used to destabilize target transcripts and/or block their translation (e.g., PTB expression). Exemplary coding sequences for PTB-shRNA include SEQ ID NO:2 and 3. It should be noted that SEQ ID NO:2 and 3 are depicted as DNA, however, it should be noted that "T" can be replaced with "U" to arrive at an RNA sequence. Such DNA and RNA sequences can be part of vectors used in the methods and compositions of the disclosure.

In some embodiments, a plasmid containing a DNA sequence encoding a particular desired siRNA sequence is delivered into a target cell via transfection or virally-mediated infection. Once in the cell, the DNA sequence is continuously transcribed into RNA molecules that loop back on themselves and form hairpin structures through intramolecular base pairing. These hairpin structures, once processed by the cell, are equivalent to transfected siRNA molecules and are used by the cell to mediate RNAi of the desired protein. The use of shRNA has an advantage over siRNA transfection as the former can lead to stable, long-term inhibition of protein expression. Inhibition of protein expression by transfected siRNAs is a transient phenomenon that does not occur for times periods longer than several days. In some cases, this can be useful and desired. In cases where longer periods of protein inhibition are necessary, shRNA-mediated inhibition can be used. Short Hairpin RNAs (shRNA) can be comprised of stem-loop structures, which can be designed to contain a 5' flanking region, siRNA region segments, a loop region, a 3' siRNA region and a 3' flanking region. shRNAs can have effective knockdown of target sequences. In some embodiments the DNA sequence encoding shRNA against human PTB comprises the following sequence (SEQ ID NO:2):

5'-GCGTGAAGATCCTGTTCAATA*CTCGAG*TATTGAACAGGATCTTCACGC-3'

The sense part, loop and antisense part are shown in bold, italics, and underline, respectively. In some embodiments, the DNA sequence encoding shRNA against mouse PTB (SEQ ID NO:3):

5'-GGGTGAAGATCCTGTTCAATA*CTCGAG*TATTGAACAGGATCTTCACCC-3'

The sense part, loop and antisense part are shown in bold, italics, and underline, respectively.

Sponge polynucleotides that have a base sequence complementary to part or all of target RNA transcript (e.g., PTB mRNA transcript) can be used in the method provided herein as well. For instance, sponge polynucleotide can contain polypyrimidine tract. Sponge polynucleotides can be used to "trap" PTB mRNA transcripts, thereby blocking them from being normally spliced, translated, or transported, so that the expression level of PTB protein can be reduced.

In some cases, the PTB inhibition agent can be a dominant-negative mutant that can inhibit an activity of PTB molecule. The dominant negative mutant can be a peptide or peptide mimetic that can inhibit an activity of PTB molecule, or a nucleic acid composition, in the form of a DNA vector or gene therapy vector, that expresses a dominant-negative polypeptide that can inhibit an activity of PTB. The dominant negative mutant can bind to a target RNA or ligand of PTB, affecting its target interaction. The dominant negative molecule can act, for example, by blocking protein-protein interactions or protein-RNA interactions.

Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, e.g., to induce or stabilize a secondary structure, e.g., a beta turn, gamma turn, beta sheet, alpha helix conformation, and the like. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(═O)—CH2— for —C(═O)—NH—), aminomethylene (CH2-NH), ethylene, olefin (CH═CH), ether (CH2-O), thioether (CH2-S), tetrazole (CN4-), thiazole, retroamide, thioamide, or ester.

Another non-limiting example of a PTB inhibition agent can be anti-PTB antibody. An anti-PTB antibody can be a polyclonal antibody or a monoclonal antibody that specifically binds to PTB. An anti-PTB antibody as used herein can bind to PTB at its active fragment or inactive fragment. In some configurations, an anti-PTB antibody that binds to the active fragment of PTB can block PTB from interacting with its functional targets (e.g., target RNA transcript) or partners (e.g., protein ligands), thereby inhibiting activity of PTB. In other configurations, an anti-PTB antibody that binds to the inactive fragment of PTB can induce PTB aggregation in some cases, thereby immobilizing PTB inside the cell, preventing it from relocating to interact with its targets or partners. In some cases, an anti-PTB antibody can also induce protein degradation of PTB as being bound to an antibody.

Antisense nucleic acids (e.g., DNA, RNA, modified DNA, or modified RNA) are generally single-stranded nucleic acids complementary to a portion of a target nucleic acid (e.g., a PTB mRNA transcript) and therefore able to bind to the target to form a duplex. An anti-PTB antisense nucleotide can be configured to suppress the expression or activity of PTB, e.g., in a cell. Antisense oligonucleotides (ASOs) can pair with a target mRNA to render the RNA a substrate for cleavage by the intranuclear enzyme RNase H. In some cases, antisense oligonucleotide can mediate target mRNA degradation for ~3 months in the nervous system, e.g., the rodent and non-human primate nervous system after injection into the cerebral spinal fluid. As provided herein, antisense oligonucleotide that can be used in the methods provided herein are typically oligonucleotides that range from 15 to 35 nucleotides in length but can range from 10 up to approximately 50 nucleotides in length. Binding can reduce or inhibit the function of the target PTB nucleic acid. For example, antisense oligonucleotides can block transcription when bound to genomic DNA (e.g., PTB gene), inhibit translation when bound to mRNA (e.g., PTB mRNA transcript), and/or lead to degradation of the nucleic acid. Reduction in expression of PTB can be achieved by the administration of antisense nucleic acids or peptide nucleic acids comprising sequences complementary to those of the mRNA that encodes the polypeptide. Antisense technology and its applications are well known in the art and are described in (Phillips, M. I. (ed.) Antisense Technology, Methods Enzymol., 313, Bennett, C. F., Krainer, A. R. and Cleveland, D. W. (2019). Antisense oligonucleotide therapies for neurodegenerative diseases. Ann. Rev. Neurosci. 42, 385-406, and 314: 2000, and references mentioned therein. See also Crooke, S. "ANTISENSE DRUG TECHNOLOGY: PRINCIPLES, STRATEGIES, AND APPLICATIONS" (1st Edition) Marcel Dekker; and references cited therein. In some cases, antisense oligonucleotide as provided herein can comprise locked nucleic acids (LNAs). In some cases, LNAs refer to a modified RNA nucleotide, in which the ribose moiety is modified with an extra bridge connecting the 2' oxygen and 4' carbon and the bridge "locks" the ribose in the 3'-endo (North) conformation. In some cases, LNAs are be mixed with DNA or RNA residues in the oligonucleotide whenever desired and hybridize with DNA or RNA according to Watson-Crick base-pairing rules. The locked ribose conformation can enhance base stacking and backbone pre-organization. Inclusion of LNAs in the oligonucleotide as provide herein, in some cases, increases the hybridization properties (melting temperature) of oligonucleotides. In some cases, inclusion of LNAs blocks translation of the target mRNA, but without inducing degradation of the target mRNA. Exemplary techniques and applications of using LNAs can be found in PCT/US2013/047157 and Campbell M A et al., Chem. Soc. Rev., 40(12), 5680-9, which are incorporated herein by reference in their entireties.

The PTB inhibition agent as provided herein can also include ribozymes or deoxyribozymes that can catalyze the sequence-specific cleavage of RNA molecules. The cleavage site is determined by complementary pairing of nucleotides in the RNA or DNA enzyme with nucleotides in the target RNA (e.g., PTB mRNA transcript). Thus, RNA and DNA enzymes can be designed to cleave PTB mRNA transcript, thereby increasing its rate of degradation.

In certain instances, the PTB inhibition agent suppresses or reduces the expression or activity of PTB by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the endogenous or native level. As provided herein, the PTB inhibition agent suppresses expression or activity of PTB by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100% of the level without the PTB inhibition agent. In some cases, a PTB inhibition agent as provided herein directly suppress the expression level of PTB, e.g., suppressing the transcription, translation, or protein stability of PTB. In some cases, PTB inhibition agent as provided herein directly suppresses the activity of PTB, e.g., blocking the binding of PTB to its target molecules. In some cases, the PTB inhibition agent as provided herein directly effects on the expression or activity of PTB, without affecting other cellular signaling pathway.

In certain cases, the PTB inhibition agent and the miR-9 agent are encoded by an expression vector. In some embodiments, the expression vector is a viral vector. In some embodiments, the viral vector is an adenoviral, a lentiviral or an adeno-associated viral (AAV) vector. In an instance, the expression vector is a viral vector wherein the viral vector is an adeno-associated viral (AAV) vector. In some embodiments, the AAV vector is AAV2, AAV8, or AAV9. An AAV vector can comprise one or more AAV inverted terminal repeats (ITRs) flanking a polynucleotide encoding a PTB inhibition agent and/or a polynucleotide encoding an miR-9 agent. The polynucleotide can be operatively linked to transcriptional control DNAs, specifically promoter DNA and polyadenylation signal sequence DNA that are functional in target cells to form an expression cassette. The expression cassette may also include intron sequences to facilitate processing of an RNA transcript when expressed in mammalian cells. In an instance, the AAV vector comprises an AAV2, AAV8, or AAV9 vector. In an instance, the viral vector comprises the PTB inhibition agent of SEQ ID NO:2. In an instance, the viral vector comprises the miR-9 agent of SEQ ID NO: 3. In certain instances, the viral vector comprises the PTB inhibition agent of SEQ ID NO:2 and/or 3 and miR-9 agent of SEQ ID NO:1 from nucleotide 3409-3469.

The expression cassette may encode one or more anti-PTB shRNA ("shPTB") molecules and/or one or more miR-9 molecules. In some embodiments, the expression cassette contains a miR-124 sequence. In some embodiments, the expression cassette comprises a nucleotide sequence encoding a single shPTB molecule. In some embodiments, the expression cassette comprises a nucleotide sequence encoding a single miR-9 molecule. In some embodiments, the expression cassette comprises a nucleotide sequence encoding a single shPTB and a single miR-9. In some embodiments, the expression cassette comprises a nucleotide sequence encoding two or three shPTB molecules. In some embodiments, the expression cassette comprises a nucleotide sequence encoding two or three miR-9 molecules. In some embodiments, the expression cassette comprises a nucleotide sequence encoding one, two or three miR-124 molecules. In some embodiments, the expression cassette comprises regulatory elements to differentially express the anti-PTB shRNA and the miR-9 and the optional miR-124. In some embodiments, the regulatory element is a polIII promoter. In one embodiment, the polIII promoter is an H1 or U6 promoter.

Figure 2A:
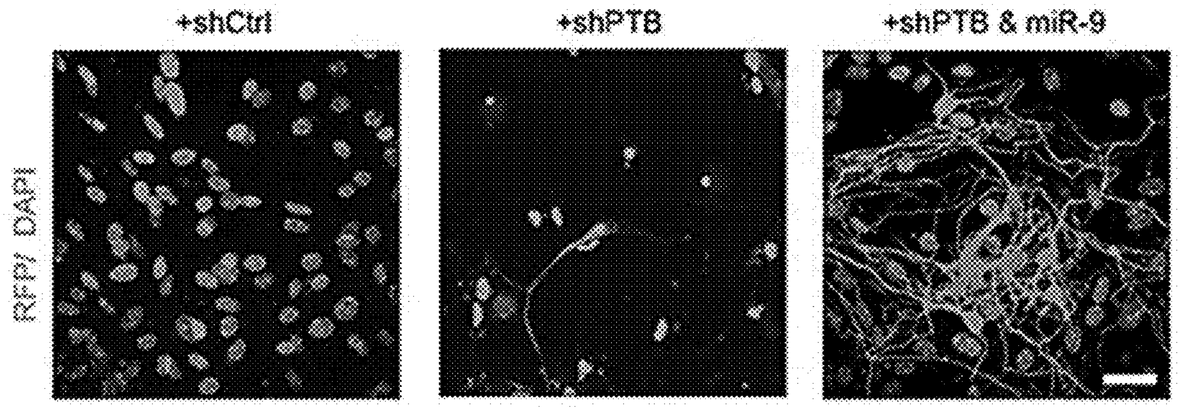
FIGS. 2A-E show exemplary data for age-restriction to neuronal reprogramming due to reduced miR-9. Astrocyte reprogramming to neurons induced by shPTB alone or in combination with miR-9 is shown in FIG. 2A.
Figure 2B:
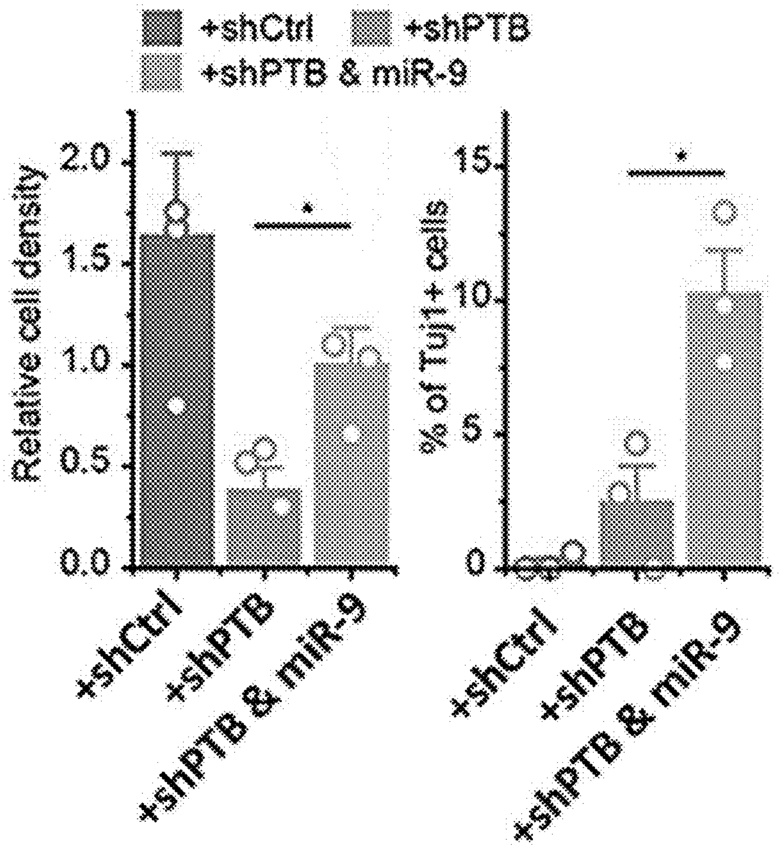
Figure 2C:
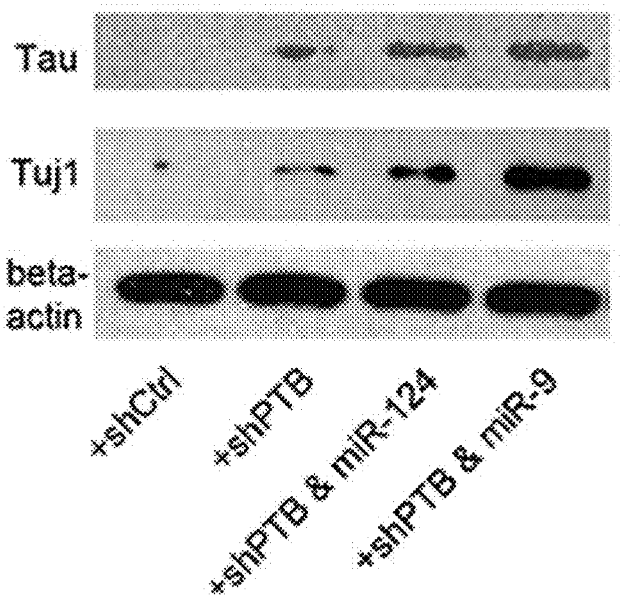
Figure 2D:
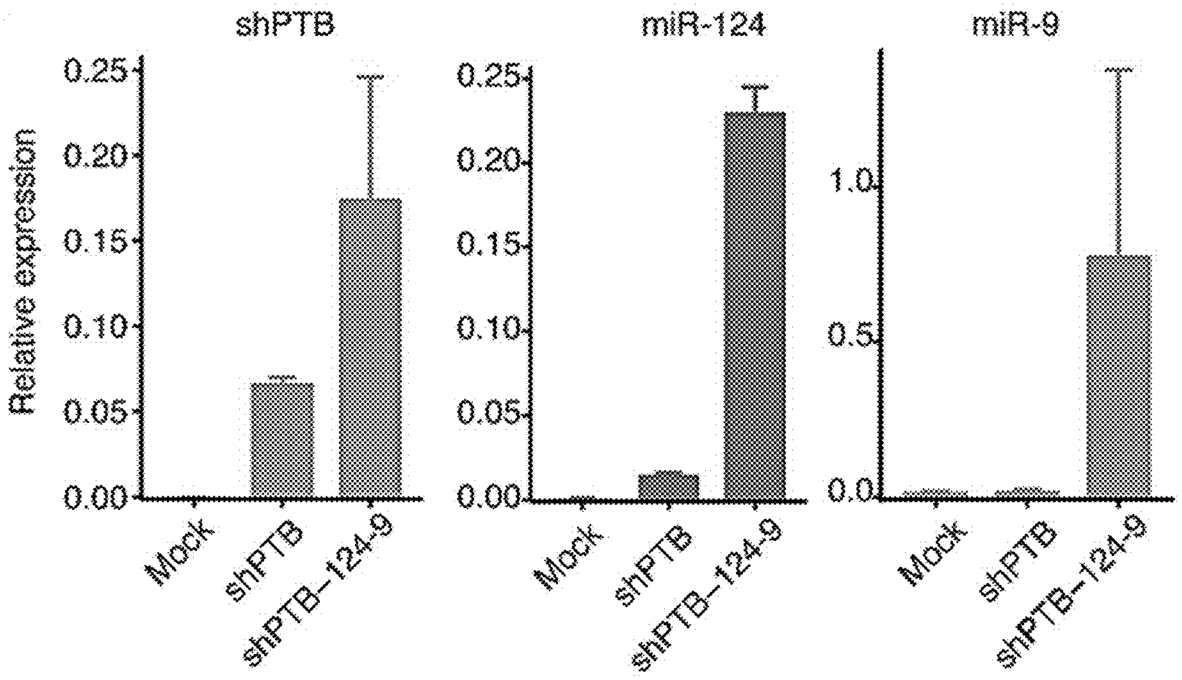
Figure 2E:
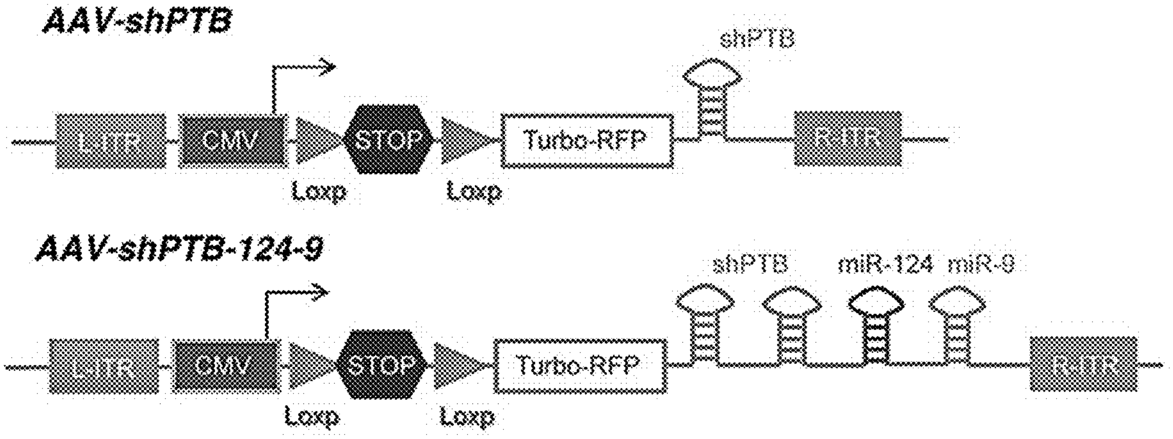
Figure 5:
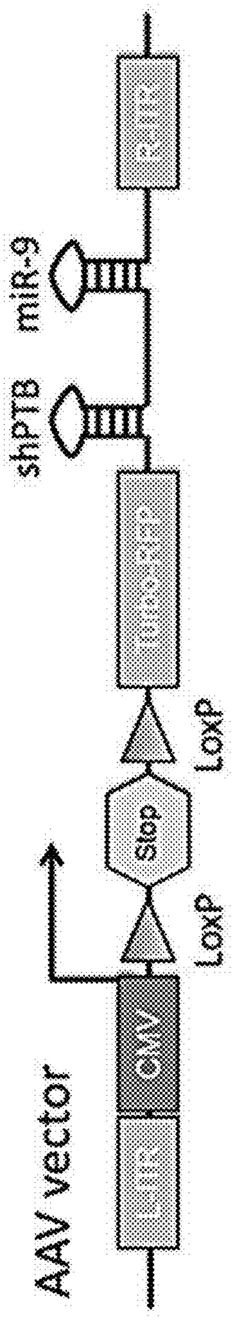
FIG. 5 shows a schematic of a construct encoding an anti-PTB shRNA and miR-9. The construct also includes inverted terminal repeats (L-ITR and R-ITR), a CMV promoter, LoxP, stop codon, LoxP, and Turbo-RFP.
Figure 6:
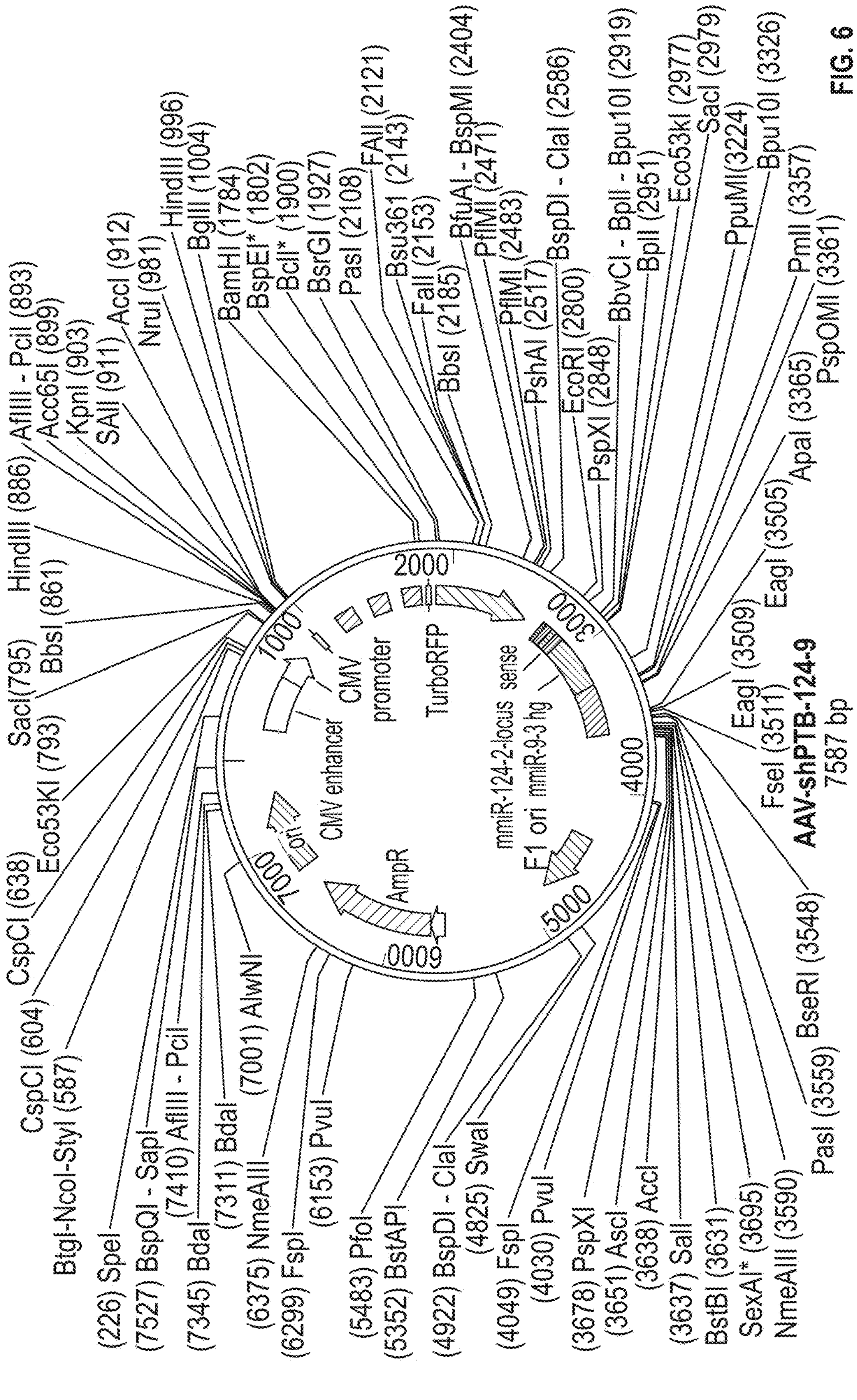
FIG. 6 provides a map of a construct of the disclosure.

In one embodiment a vector of the disclosure has the general structure of FIG. 2E or 5, wherein the vector comprises 1 or 2 shPTB coding sequences, one miR-9 coding sequence and an optional miR-124 coding sequence. In another embodiment, a vector of the disclosure comprises a sequence that is at least 85%-100% identical to SEQ ID NO:1 and has the general format of FIG. 2E, "AAV-shPTB-124-9".

In one embodiment, the disclosure provides pharmaceutical compositions comprising a PTB inhibition agent and an miR-9 agent and an optional miR-124 molecule in an amount effective to reprogram an age restricted non-neuronal cell to a mature neuron by suppressing the expression or activity of PTB and increasing the miR-9 expression or activity in the non-neuronal cell. An exemplary pharmaceutical composition can further comprise a pharmaceutically acceptable carrier or excipient. As described above, a PTB inhibition agent and/or an miR-9 agent as provided herein can be a small chemical molecule, interfering RNA, short hairpin RNA, microRNA, dominant negative mutant, ribozyme, antisense oligonucleotide, protein inhibitor, monoclonal antibody, a polyclonal antibody, a peptide, or any form of modified nucleic acid.

A pharmaceutical composition provided herein can include one or more carriers and excipients (including but not limited to buffers, carbohydrates, mannitol, proteins, peptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In another instance, the composition is substantially free of preservatives. In other embodiments, the composition contains at least one preservative. General methodology on pharmaceutical dosage forms can be found in Ansel et ah, Pharmaceutical Dosage Forms and Drug Delivery Systems (Lippencott Williams & Wilkins, Baltimore Md. (1999)). It will be recognized that, while any suitable carrier known to those of ordinary skill in the art can be employed to administer the pharmaceutical compositions described herein, the type of carrier can vary depending on the mode of administration. Suitable formulations and additional carriers are described in Remington "The Science and Practice of Pharmacy" (20th Ed., Lippincott Williams & Wilkins, Baltimore Md.), the teachings of which are incorporated by reference in their entirety herein. An exemplary pharmaceutical composition can be formulated for injection, parenteral administration, intravenous administration, or injection into the CSF. As one of ordinary skills in the art will appreciate, pharmaceutical compositions can comprise any appropriate carrier or excipient, depending on the type of PTB inhibition agent and miR-9 agent and the administration route the composition is designed for. For example, a composition comprising a PTB inhibition agent and miR-9 agent as provided herein can be formulated for parenteral administration and can be presented in unit dose form in ampoules, pre-filled syringes, small volume infusion or in multidose containers with an added preservative. The composition can take such forms as suspensions, solutions, or emulsions in oily or aqueous vehicles, for example solutions in aqueous polyethylene glycol. For example. for injectable formulations, a vehicle can be chosen from those known in the art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of active agent in injection grade water, liposomes, and vehicles suitable for lipophilic substances and those known in the art. A composition as provided herein can further comprise additional agent besides a PTB inhibition agent and miR-9 agent and a pharmaceutically acceptable carrier or excipient. For example, additional agent can be provided for promoting neuronal survival purpose. Alternatively or additionally, additional agent can be provided for monitoring pharmacodynamics purpose. In some embodiments, a composition comprises additional agent as a penetration enhancer for delivery of constructs comprising, e.g., PTB inhibition agent and miR-9 agent and optional miR-124 molecules.

Disclosed herein are methods for reprogramming a non-neuronal cell into a neuron, wherein the method comprises contacting the non-neuronal cell with the composition comprising a PTB inhibition agent and an miR-9 agent thereby reprogramming the non-neuronal cell into the neuron.

In some embodiments, a therapeutically effective amount of composition is administered to the non-neuronal cell. A "therapeutically effective amount" of a composition of the disclosure will vary according to factors such as the disease state, age, sex, and weight of the individual, and the ability of the composition to elicit a desired response in the individual, the formulation or type of agent being delivered, etc. A therapeutically effective amount can also be one in which any toxic or detrimental effects of the composition are outweighed by the therapeutically beneficial effects. Without wishing to be bound by a particular theory, it is contemplated that, in some cases, a therapeutically effective amount of composition comprising a PTB inhibition agent and an miR-9 agent and an optional miR-124 molecule as provided herein can be an amount that converts a certain proportion of astrocytes in a brain region that experiences neuronal loss, conversion of such proportion of astrocytes to functional neurons in the brain region is sufficient to ameliorate or treating the disease or condition associated with the neuronal loss in the brain region, and meanwhile, such proportion of astrocytes does not exceed a threshold level that can lead to adverse effects that can outweigh the beneficial effects brought by the neuronal conversion, for instance, due to excessive reduction in the number of astrocytes in the brain region as a direct consequence of the neuronal conversion. In some embodiments, a therapeutically effective amount of the composition is an amount sufficient to inhibit PTB expression or activity and/or increase miR-9 expression or activity. A sufficient amount of composition can be determined empirically as one skilled in the art would readily appreciate. In some cases, the amount of composition can be determined by any type of assay that examines the activity of the composition in the non-neuronal cell. For example, when the composition is configured to suppress the expression of PTB and increase miR-9 expression in the non-neuronal cell, the sufficient amount of the composition can be determined by assessing the expression level of PTB and/or miR-9 in an exemplary non-neuronal cell after administration of the composition, e.g., by Western blot. In some cases, functional assays are utilized for assessing the activity of PTB and/or miR-9 after delivery of the composition to an exemplary non-neuronal cell. In some cases, other functional assays, such as, immunostaining for neuronal markers, electrical recording for neuronal functional properties, that examine downstream neuronal properties are used to determine a sufficient amount of composition.

In certain cases, the non-neuronal cell is a glial cell. In certain case, the glial cell is an astrocyte. In an instance, the astrocyte expresses miR-9 at a reduced level as compared to an astrocyte of a younger age or as compared to a threshold level of expression. The term "a reduced level as compared to an astrocyte of a younger age" or "reduced level as compared to a threshold level of expression" can include instances wherein expression of miR-9 is reduced by about 20% to about 100%. In some instances, expression of miR-9 is reduced by about 20% to about 25%, about 20% to about 30%, about 20% to about 40%, about 20% to about 50%, about 20% to about 60%, about 20% to about 70%, about 20% to about 75%, about 20% to about 80%, about 20% to about 90%, about 20% to about 95%, about 20% to about 100%, about 25% to about 30%, about 25% to about 40%, about 25% to about 50%, about 25% to about 60%, about 25% to about 70%, about 25% to about 75%, about 25% to about 80%, about 25% to about 90%, about 25% to about 95%, about 25% to about 100%, about 30% to about 40%, about 30% to about 50%, about 30% to about 60%, about 30% to about 70%, about 30% to about 75%, about 30% to about 80%, about 30% to about 90%, about 30% to about 95%, about 30% to about 100%, about 40% to about 50%, about 40% to about 60%, about 40% to about 70%, about 40% to about 75%, about 40% to about 80%, about 40% to about 90%, about 40% to about 95%, about 40% to about 100%, about 50% to about 60%, about 50% to about 70%, about 50% to about 75%, about 50% to about 80%, about 50% to about 90%, about 50% to about 95%, about 50% to about 100%, about 60% to about 70%, about 60% to about 75%, about 60% to about 80%, about 60% to about 90%, about 60% to about 95%, about 60% to about 100%, about 70% to about 75%, about 70% to about 80%, about 70% to about 90%, about 70% to about 95%, about 70% to about 100%, about 75% to about 80%, about 75% to about 90%, about 75% to about 95%, about 75% to about 100%, about 80% to about 90%, about 80% to about 95%, about 80% to about 100%, about 90% to about 95%, about 90% to about 100%, or about 95% to about 100%. In some instances, expression of miR-9 is reduced by about 20%, about 25%, about 30%, about 40%, about 50%, about 60%, about 70%, about 75%, about 80%, about 90%, about 95%, or about 100%. In some instances, expression of miR-9 is reduced by at least about 20%, about 25%, about 30%, about 40%, about 50%, about 60%, about 70%, about 75%, about 80%, about 90%, or about 95%.

In an instance, the astrocyte expresses miR-9 at a reduced level as compared to a housekeeping or constitutively expressed gene. The term "housekeeping gene" can refer to genes involved in the maintenance of basal cellular functions that are essential for the existence of a cell. Non-limiting example of housekeeping genes can include ACTB, GAPDH, TBP, RRN18S, etc. The term "a reduced level as compared to a housekeeping or constitutively expressed gene" can include instances wherein expression of miR-9 is reduced by about 20% to about 100%. In some instances, expression of miR-9 is reduced by about 20% to about 25%, about 20% to about 30%, about 20% to about 40%, about 20% to about 50%, about 20% to about 60%, about 20% to about 70%, about 20% to about 75%, about 20% to about 80%, about 20% to about 90%, about 20% to about 95%, about 20% to about 100%, about 25% to about 30%, about 25% to about 40%, about 25% to about 50%, about 25% to about 60%, about 25% to about 70%, about 25% to about 75%, about 25% to about 80%, about 25% to about 90%, about 25% to about 95%, about 25% to about 100%, about 30% to about 40%, about 30% to about 50%, about 30% to about 60%, about 30% to about 70%, about 30% to about 75%, about 30% to about 80%, about 30% to about 90%, about 30% to about 95%, about 30% to about 100%, about 40% to about 50%, about 40% to about 60%, about 40% to about 70%, about 40% to about 75%, about 40% to about 80%, about 40% to about 90%, about 40% to about 95%, about 40% to about 100%, about 50% to about 60%, about 50% to about 70%, about 50% to about 75%, about 50% to about 80%, about 50% to about 90%, about 50% to about 95%, about 50% to about 100%, about 60% to about 70%, about 60% to about 75%, about 60% to about 80%, about 60% to about 90%, about 60% to about 95%, about 60% to about 100%, about 70% to about 75%, about 70% to about 80%, about 70% to about 90%, about 70% to about 95%, about 70% to about 100%, about 75% to about 80%, about 75% to about 90%, about 75% to about 95%, about 75% to about 100%, about 80% to about 90%, about 80% to about 95%, about 80% to about 100%, about 90% to about 95%, about 90% to about 100%, or about 95% to about 100%. In some instances, expression of miR-9 is reduced by about 20%, about 25%, about 30%, about 40%, about 50%, about 60%, about 70%, about 75%, about 80%, about 90%, about 95%, or about 100%. In some instances, expression of miR-9 is reduced by at least about 20%, about 25%, about 30%, about 40%, about 50%, about 60%, about 70%, about 75%, about 80%, about 90%, or about 95%.

In certain cases, the non-neuronal cell and the neuron are located within a brain of a subject. In some embodiment, the non-neuronal cell is in the substantia nigra. In some embodiments, the composition is administered to a brain region selected from the substantial nigra, the midbrain, the basal forebrain, and the ventral tegmental area. In some embodiments, the composition is administered into substantial nigra (SN). In some embodiments, the composition is administered to ventral tegmental area (VTA). In some embodiments, the composition is administered to a region defined by a local degeneration or loss of functional neurons resulting from a disorder or trauma.

In certain instances, the subject has a neurodegenerative disorder, such as an age-related neurodegenerative disorder. In certain cases, the functional neuron is generated in a subject having a neurodegenerative disorder. In an instance, the subject comprises a neurodegenerative disorder. In some embodiments, the neurodegenerative disorder is an age-related disorder. In certain instances, the neurodegenerative disorder can be Alzheimer's Disease, Parkinson's Disease, dementia, or a disease associated with a loss of functional neurons within the brain of a subject. In some embodiments, the neurodegenerative disorder is Alzheimer's Disease. In some embodiments, the neurodegenerative disorder is Parkinson's Disease. In some embodiments, the neurodegenerative disorder or trauma is stroke or cerebrovascular accident (CVA).

Disclosed are methods for reprogramming a non-neuronal cell into a neuron, wherein the method comprises contacting the non-neuronal cell with a PTB inhibition agent that suppresses PTB expression or activity and a miR-9 agent that increases miR-9 expression or activity in the non-neuronal cell, thereby reprogramming the non-neuronal cell into the neuron. In some cases, the non-neuronal cell is a glial cell that expresses reduced levels of miR-9. In certain cases, the non-neuronal cell is a glial cell. In certain case, the glial cell is an astrocyte. In an instance, the astrocyte expresses miR-9 at a reduced level as compared to an astrocyte of a younger age.

In some embodiments, the glial cell is selected from the group consisting of an astrocyte, an oligodendrocyte, an ependymal cell, a Schwan cell, a NG2 cell, and a satellite cell. In some embodiments the glial cell is an astrocyte.

In some embodiments, the PTB inhibition agent reduces or inhibits an expression level of a nucleic acid encoding a PTB polypeptide within the non-neuronal cell. In some embodiments, the PTB inhibition agent reduces or inhibits an activity of a PTB polypeptide within the non-neuronal cell. In some embodiments, the PTB inhibition agent reduces an amount of a PTB polypeptide within the non-neuronal cell. In some cases, the PTB inhibition agent is an anti-PTB inhibitor. In certain instances, the anti-PTB inhibitor comprises an antisense oligonucleotide (ASO), an anti-PTB shRNA, an anti-PTB antibody or fragment thereof, an anti-PTB nanobody, an anti-PTB affibody, an anti-PTB polypeptide, an anti-PTB small molecule, a dominant negative PTB mutant, a PTB miRNA, or a sponge polyribonucleotide containing polypyrimidine.

In some embodiments, the miR-9 agent increases an amount of a nucleic acid encoding for a miR-9 molecule within the non-neuronal cell. In some embodiments, the miR-9 agent is a miR-9 ribonucleic acid molecule within the non-neuronal cell. In some embodiments, wherein the miR-9 agent inhibits the expression or activity of an nPTB molecule within the non-neuronal cell. In some cases, the miR-9 agent is an anti-nPTB inhibitor. In certain embodiments, the anti-nPTB inhibitor comprises an anti-nPTB shRNA, an anti-nPTB antisense oligonucleotide, an anti-nPTB antibody or fragment thereof, an anti-nPTB nanobody, an anti-nPTB affibody, an anti-nPTB polypeptide, an anti-nPTB small molecule, a dominant negative nPTB mutant, a nPTB miRNA, or a sponge polyribonucleotide containing polypyrimidine.

In some embodiments, a level of PTB expression or activity is reduced for an extended period of time. In certain instances, the level of PTB expression and/or activity is reduced for at least about 0.5 days to about 15 days. In certain embodiments, the level of PTB expression and/or activity is reduced for at least about 0.5 days to about 1 day, about 0.5 days to about 2 days, about 0.5 days to about 4 days, about 0.5 days to about 5 days, about 0.5 days to about 10 days, about 0.5 days to about 12 days, about 0.5 days to about 15 days, about 1 day to about 2 days, about 1 day to about 4 days, about 1 day to about 5 days, about 1 day to about 10 days, about 1 day to about 12 days, about 1 day to about 15 days, about 2 days to about 4 days, about 2 days to about 5 days, about 2 days to about 10 days, about 2 days to about 12 days, about 2 days to about 15 days, about 4 days to about 5 days, about 4 days to about 10 days, about 4 days to about 12 days, about 4 days to about 15 days, about 5 days to about 10 days, about 5 days to about 12 days, about 5 days to about 15 days, about 10 days to about 12 days, about 10 days to about 15 days, or about 12 days to about 15 days. In certain embodiments, the level of PTB expression and/or activity is reduced for at least about 0.5 days, about 1 day, about 2 days, about 4 days, about 5 days, about 10 days, about 12 days, or about 15 days. In certain embodiments, the level of PTB expression and/or activity is reduced for at least at least about 0.5 days, about 1 day, about 2 days, about 4 days, about 5 days, about 10 days, or about 12 days. In certain instances, the level of PTB expression and/or activity is reduced for at least at most about 1 day, about 2 days, about 4 days, about 5 days, about 10 days, about 12 days, or about 15 days.

In some embodiments, the miR-9 agent increases a level of miR-9 expression or activity for an extended period of time. In certain embodiments, the level of miR-9 expression and/or activity is increased for at least about 0.5 days to about 15 days. In certain embodiments, the level of miR-9 expression and/or activity is increased for at least about 0.5 days to about 1 day, about 0.5 days to about 2 days, about 0.5 days to about 4 days, about 0.5 days to about 5 days, about 0.5 days to about 10 days, about 0.5 days to about 12 days, about 0.5 days to about 15 days, about 1 day to about 2 days, about 1 day to about 4 days, about 1 day to about 5 days, about 1 day to about 10 days, about 1 day to about 12 days, about 1 day to about 15 days, about 2 days to about 4 days, about 2 days to about 5 days, about 2 days to about 10 days, about 2 days to about 12 days, about 2 days to about 15 days, about 4 days to about 5 days, about 4 days to about 10 days, about 4 days to about 12 days, about 4 days to about 15 days, about 5 days to about 10 days, about 5 days to about 12 days, about 5 days to about 15 days, about 10 days to about 12 days, about 10 days to about 15 days, or about 12 days to about 15 days. In certain instances, the level of miR-9 expression and/or activity is increased for at least about 0.5 days, about 1 day, about 2 days, about 4 days, about 5 days, about 10 days, about 12 days, or about 15 days. In certain instances, the level of miR-9 expression and/or activity is increased for at least about 0.5 days, about 1 day, about 2 days, about 4 days, about 5 days, about 10 days, or about 12 days.

In some embodiments, the non-neuron cell is located within a brain region of a mammal. In an instance, the mammal is a human. In some embodiments, the subject comprises a phenotype wherein contacting the non-neuronal cell within the brain of the subject with the PTB inhibition agent alone does not reprogram the non-neuronal cell into a functional neuron. In some embodiments, the subject is an elderly individual with a brain injury or an individual with an age-related neurodegenerative disorder. In some embodiments, the elderly individual is over 50 years of age, or over 55 years of age, or over 60 years of age, or over 65 years of age, or over 70 years of age, or over 75 years of age.

The disclosure further provides a method of generating a neuron within a subject, wherein the method comprises administering a PTB inhibition agent that suppresses PTB expression or activity and a miR-9 agent that increases miR-9 expression or activity in the non-neuronal cell and an optional miR-124 molecule to a brain region that comprises a non-neuronal cell that expresses miR-9 at a reduced level as compared to a non-neuronal cell from the same brain region of a younger subject, thereby reprogramming the non-neuronal cell into the neuron. In some embodiments, the neuron is a dopaminergic neuron or a cholinergic neuron. In some embodiments, the non-neuronal cell is a glial cell that expresses miR-9. In some cases, the glial cell is selected from the group consisting of an astrocyte, an oligodendrocyte, an ependymal cell, a Schwan cell, NG2 cell, and a satellite cell. In certain instances, the glial cell is an astrocyte. In certain instances, the subject is a human and the younger subject can be a young mouse. In some cases, the PTB inhibition agent reduces or inhibits an expression level of a nucleic acid encoding a PTB polypeptide within the non-neuronal cell. In some cases, the PTB inhibition agent reduces or inhibits an activity of a PTB polypeptide within the non-neuronal cell. In some embodiments, the PTB inhibition agent reduces an amount of a PTB polypeptide within the non-neuronal cell. In some cases, the PTB inhibition agent is an anti-PTB inhibitor.

In some embodiment, the method comprises administering a construct of SEQ ID NO:1 to a brain region of the subject to produce neuron(s) in the subject from non-neuronal cells. In one embodiment, the construct of SEQ ID NO:1 is delivered by an AAV capsid.

In some embodiments, the subject is an elderly individual with a brain injury or an individual with an age-related neurodegenerative disorder.

In some embodiments, the PTB inhibition agent and miR-9 agent and an optional miR-124 molecule are contacted to a non-neuronal cell by delivery in the form of a viral vector. A viral vector can comprise one or more copies of an expression construct encoding a PTB inhibition agent, miR-9 agent and optional miR-124 molecule, e.g., shRNA, ASO, microRNA, dominant negative mutant, or antibody, such as, 1, 2, 3, 4, 5, 6, 7, 8, 9, 10, 20, 30, 50, or 100 copies. A viral vector can be titered to any appropriate amount for administration, as one skilled in the art will be able to determine. For example, the titer as determined by PCR, RT-PCR, or other methods can be at least about $10^5$ viral particles/mL, at least about $10^6$ particles/mL, at least about $10^7$ particles/mL, at least about $10^8$ particles/mL, at least about $10^9$ particles/mL, at least about $10^{10}$ particles/mL, at least about $10^{11}$ particles/mL, at least about $10^{12}$ particles/mL, at least about $10^{13}$ particles/mL, at least about $10^{14}$ particles/mL, or at least about $10^{15}$ particles/mL. In some cases, the titer of viral vector to be administered is at least about $10^{10}$ viral particles/mL. In one embodiment, the vector comprises the sequence of SEQ ID NO:1 and is contained in an AAV capsid. In some cases, the composition is antisense oligonucleotide, and the antisense oligonucleotide can be delivered at any effective amount as one skilled in the art will appreciate. In certain cases, the antisense oligonucleotide can be administered at least about 0.05 μg, at least about 0.075 μg, at least about 0.1 μg, at least about 0.125 μg, at least about 0.15 μg, at least about 0.175 μg, at least about 0.2 μg, at least about 0.225 μg, at least about 0.25 μg, at least about 0.275 μg, at least about 0.3 μg, at least about 0.325 μg, at least about 0.35 μg, at least about 0.375 μg, at least about 0.4 μg, at least about 0.425 μg, at least about 0.045 μg, at least about 0.475 μg, at least about 0.5 μg, at least about 0.6 μg, at least about 0.7 μg, at least about 0.8 μg, at least about 0.9 μg, at least about 1.0 μg, at least about 1.2 μg, at least about 1.25 μg, at least about 1.3 μg, at least about 1.4 μg, at least about 1.5 μg, at least about 1.6 μg, at least about 1.7 μg, at least about 1.8 μg, at least about 1.9 μg, at least about 2.0 μg, at least about 2.1 μg, at least about 2.2 μg, at least about 2.3 μg, at least about 2.4 μg, at least about 2.5 μg, at least about 2.75 μg, at least about 3 μg, at least about 4 μg, at least about 5 μg, at least about 6 μg, at least about 7 μg, at least about 8 μg, at least about 9 μg, or at least about 10 μg. In some embodiments, the antisense oligonucleotide is administered about 0.05 μg, about 0.075 μg, about 0.1 μg, about 0.125 μg, about 0.15 μg, about 0.175 μg, about 0.2 μg, about 0.225 μg, about 0.25 μg, about 0.275 μg, about 0.3 μg, about 0.325 μg, about 0.35 μg, about 0.375 μg, about 0.4 μg, about 0.425 μg, about 0.045 μg, about 0.475 μg, about 0.5 μg, about 0.6 μg, about 0.7 μg, about 0.8 μg, about 0.9 μg, about 1.0 μg, about 1.2 μg, about 1.25 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.75 μg, about 3 μg, about 4 μg, about 5 μg, about 6 μg, about 7 μg, about 8 μg, about 9 μg, or about 10 μg. In some cases, the antisense oligonucleotide is administered in vitro at about 0.075 to about 0.325 μg, about 0.1 to about 0.3 μg, or about 0.125 to about 0.25 μg. In some cases, the antisense oligonucleotide is administered in vivo at about 1 to about 10 μg, at about 1 to about 5 μg, at about 1 to about 3 μg, about 1.5 to about 2.5 μg, or about 1.75 to about 2.25 μg.

A PTB inhibition agent, a miR-9 agent and an optional miR-124 molecule can be delivered directly to the brain or by systemic injection into a subject. In some embodiments, a composition comprising the PTB inhibition agent and the miR-9 agent with or without a miR-124 molecule is administered or delivered to the central nervous system. Methods of therapeutic delivery to the central nervous system and the brain is appreciated and understood to one skilled in the art. In another embodiment, a composition as provided herein is delivered systemically to a subject or to a region in nervous system, e.g., brain or spinal cord, of a subject, e.g., delivered to cerebrospinal fluid or cerebral ventricles. In some embodiments, the administration is to the brain or a region of the brain. In some embodiments, the administration is to the substantial nigra. In some embodiments, the administration is to the midbrain. In some embodiments, the administration is to the basal forebrain. In some embodiments, the composition is administered to the cerebrospinal fluid (CSF). In some embodiments, the administration is via intracranial injection, intracerebroventricular injection, intracisternal injection, or intrathecal injection. In some embodiments, administration is via intravenous injection. In some embodiments, administration is via retro-orbital injection.

Figure 3:
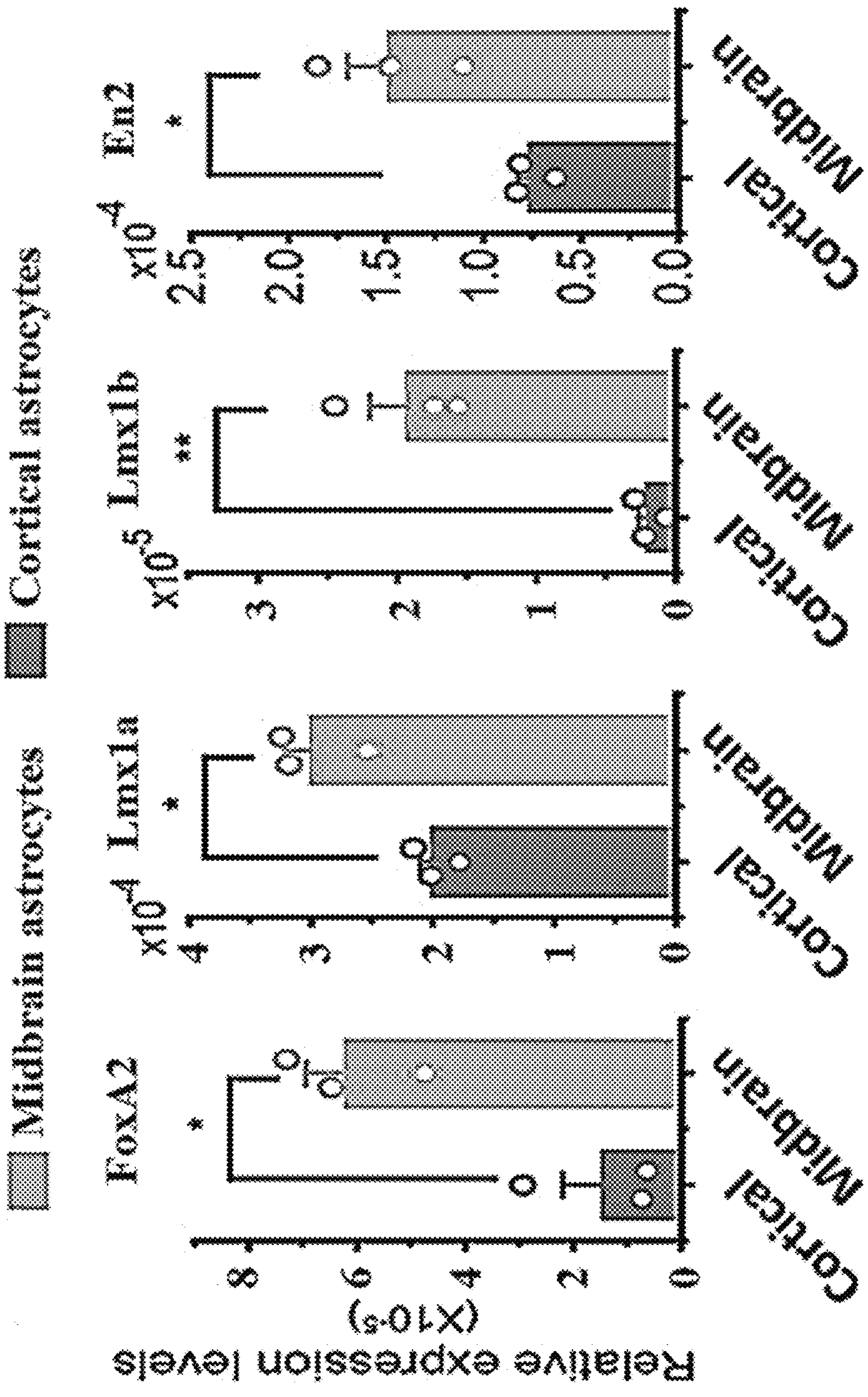
FIG. 3 shows exemplary data for expression of neuronal specific transcription factors in different astrocytes from different regions of the brain. The selective subset of TFs was analyzed by real time RT-PCR. The data were normalized against actin.
Figure 4:
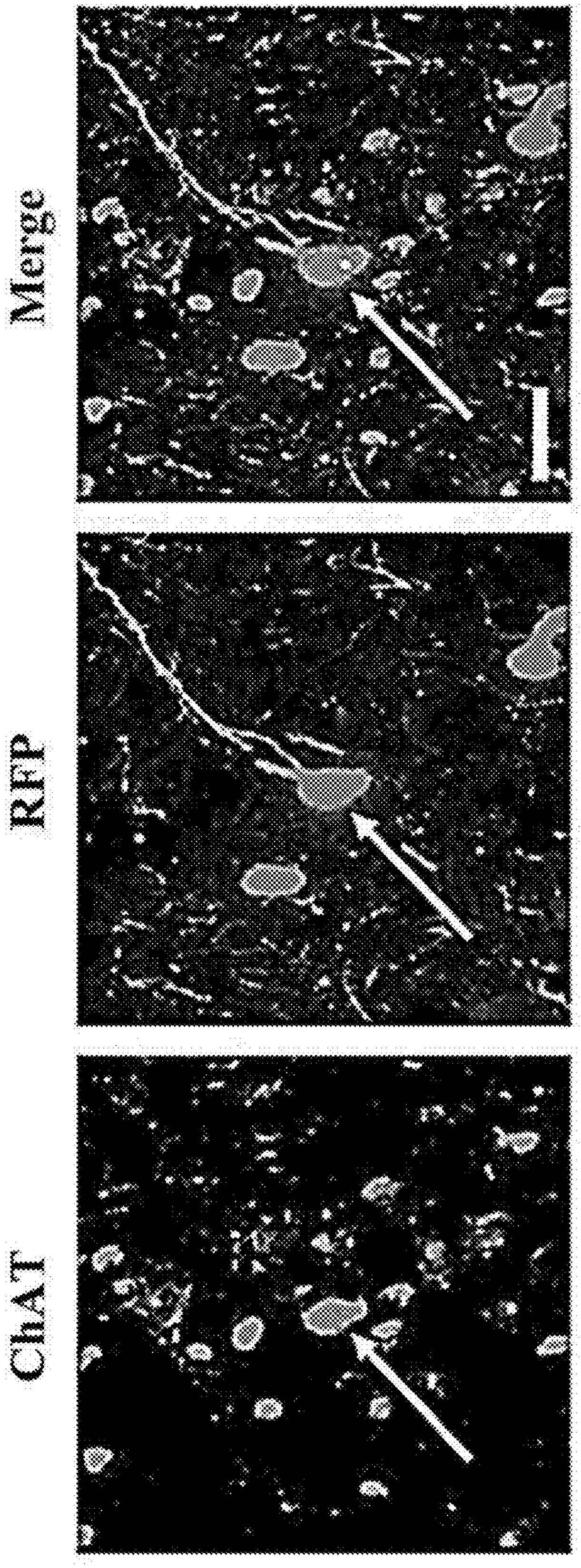
FIG. 4 shows exemplary data demonstrating the region specific conversion of astrocytes to neurons. Targeting astrocytes within the basal forebrain results in the generation of cholinergic neurons.

Also disclosed herein are methods for generating function-specific neurons within the brain of a subject. A function-specific neuron can be a specific type of neuron (e.g., dopaminergic, cholinergic, etc.) or a function-specific neuron can be a neuron having a specific, intended function (e.g., release of a specific neurotransmitter, neurons comprising a specific phenotype, etc.). FIG. 3 demonstrates the molecular basis for regional specificity in non-neuronal cells. Shown are examples of region-specific transcription profiles in astrocytes from the midbrain and cortical region of the brain. The differential, region-specific transcription program phenotypes can potentiate the ability of astrocytes to be reprogrammed into specific types of neurons and/or function-specific neurons. FIG. 4 demonstrates an example targeting the regional specificity of non-neuronal cells to generate a function-specific neuron, specifically, astrocytes within the basal forebrain can be reprogrammed into cholinergic neurons, which originate from the basal forebrain region.

Disclosed are methods of generating a neuron within a brain of a subject, wherein the method comprises contacting a non-neuronal cell that is located within a region of the brain that the functional neuron originates from with a PTB inhibition agent that suppresses PTB expression or activity, thereby reprogramming the non-neuronal cell into the neuron. In some cases, the method further comprises contacting a non-neuronal cell that is located within a region of the brain that the functional neuron originates with a miR-9 agent that increases miR-9 expression or activity in the non-neuronal cell. In some cases, the functional neuron comprises a transcriptional phenotype similar to the non-neuronal cell that is located within a region of the brain. In certain instances, the functional neuron is a dopaminergic neuron and the non-neuronal cell that is located within a mesencephalon region of the brain. In certain instances, the functional neuron is a cholinergic neuron and the non-neuronal cell that is located within a basal forebrain region of the brain. In some cases, the non-neuronal cell is a glial cell. In certain instances, the non-neuronal cell is an astrocyte.

Disclosed is a method of generating a functional neuron within a brain of a subject with Alzheimer's Disease, wherein the method comprises contacting a non-neuronal cell with a PTB inhibition agent that suppresses PTB expression or activity and a miR-9 agent that increases miR-9 expression or activity and optionally a miR-124 agent, thereby reprogramming the non-neuronal cell into a functional neuron, wherein the non-neuronal cell is within a region of the brain from which the functional neuron originates.

Disclosed is a method of generating a functional neuron within the brain of a subject with Parkinson's Disease, wherein the method comprises contacting a non-neuronal cell with a PTB inhibition agent that suppresses PTB expression or activity and a miR-9 agent that increases miR-9 expression or activity and optionally a miR-124 agent, thereby reprogramming the non-neuronal cell into a functional neuron wherein the non-neuronal cell is within a region of the brain from which the functional neuron originates.

Disclosed herein are kits for generating a functional neuron within a brain of a subject comprising a PTB inhibition agent that suppresses PTB expression or activity, a miR-9 agent that increases miR-9 expression or activity, and a set of instructions for administering the PTB inhibition agent and the miR-9 agent to the brain of the subject.

EXAMPLES

The following examples are included for illustrative purposes only and are not intended to limit the scope of the invention.

Example 1: Strategy to Overcome Age Restriction to Neuronal Reprogramming

Two regulatory loops were elucidated, one for neuronal conversion and the other for neuronal maturation. As provided herein expression of components in both loops were examined to determine which factors were linked to aging. Quantitative PCR analysis of key microRNAs was conducted in astrocytes derived from mice of different ages. Young astrocytes were isolated from the brain of postnatal day 5 mice. Old astrocytes were isolated from the brain of postnatal day 180 mice. miR-124 and miR-9 expression levels are shown. Interestingly, the results suggested that two microRNAs, miR-124 and miR-9, were both down-regulated during aging (FIG. 1), and suggested that the levels of these microRNAs may present barriers to neuronal reprogramming.

Because miR-124 is involved in the first loop for neuronal induction, which is suppressed by the transcription repressor REST, knockdown of PTB was expected to induce the expression of this microRNA. However, miR-9 is part of the second regulatory loop for neuronal maturation. One of the key problems in neuronal conversion experiments is cellular death during forced expression of neuronal reprogramming agents. Little is known about how to manage this problem. It was examined whether miR-9 was important in this process, and if so, if co-expression of miR-9 along PTB knockdown might help prevent cell death, thus leading to improved neuronal reprogramming efficiency. To test this hypothesis, miR-9 along with shPTB (example construct, FIG. 5) was co-expressed in astrocytes isolated from postnatal day 180, which is "old" compared to astrocytes from young mice (postnatal day 60). Interestingly, co-expression of miR-9 is able to dramatically increase the neuronal conversion efficiency in those old astrocytes (FIG. 2A). Quantitative analysis showed that both cell survival (FIG. 2B, left) and conversion efficiency (FIG. 2B, right) were significantly elevated with shPTB plus miR-9 compared to shPTB alone. Western blotting analysis showed that the two key neuronal markers Tau and Tuj1 were both greatly induced in response to PTB depletion in combination with miR-9 overexpression (FIG. 2C). These data suggested a means to overcome age-restriction to neuronal reprogramming from astrocytes.

Example 2: Molecular Basis for Regional Specificity in Astrocytes

Astrocytes from different parts of the brain appear to have intrinsic ability to develop into different neuronal subtypes once being converted. For example, astrocytes from the substantia nigra regions in midbrain are able to generate TH-positive dopaminergic neurons both in vitro and in the brain. To explore the molecular basis of this apparent regional specificity, several key transcription factors (TFs) that are uniquely expressed in dopaminergic neurons were examined, such as FOXA2, LMX1A, LMX1B, and EN2. By quantitative PCR, it was found that these TFs were essentially absent in cortical astrocytes, but readily detectable in midbrain astrocytes (FIG. 3). This finding indicated that midbrain astrocytes can inherit a key transcription program related to dopaminergic neurons because astrocytes and neurons are known to both originate from their common ancestors called radial glial cells during neurogenesis. Thus, the existing epigenetic landscape that permits detectable expression of neuronal-specific TFs may potentiate those astrocytes to develop into specific neuronal subtypes once being converted.

Example 3: The Ability to Convert Astrocytes to Cholinergic Neurons in Basal Forebrain The basal forebrain is a critical region associated with Alzheimer's disease, which has been attributed to the loss of cholinergic neurons. AAV2-shPTB vector was injected into the basal forebrain region of mice. Six weeks after AAV delivery, brain slices were stained with the cholinergic marker choline acetyltransferase (ChAT). Interestingly, detection of many RFP-marked cells was observed (because the AAV vector expresses RFP to allow lineage tracing) with a fraction of which stained positively for ChAT in the substantia innominate, which is a part of basal forebrain (FIG. 4). This observation established a foundation for region-specific targeting in generating specific types of neurons.

While certain embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCES

| SEQUENCE | ANNOTATION |
| --- | --- |
| SEQ ID NO: 1 | AAV vector comprising murine shPTB, murine miR-9 and murine miR-124 |
| GCGTGAAGATCCTGTTCAATACTC GAGTATTGAACAGGATCTTCACGC (SEQ ID NO: 2) | DNA polynucleotide sequence encoding shRNA against human PTB |
| GGGTGAAGATCCTGTTCAATACTC GAGTATTGAACAGGATCTTCACGC (SEQ ID NO: 3) | DNA polynucleotide sequence encoding shRNA against mouse PTB |
| TGGGGTTATTTTTACTTTCGGTTA TCTAGCTTTATGAAGACTCCACAC CACTCATACAGCTAGATAACCAAA GATAACAACCAACCCCG (SEQ ID NO: 4) | DNA polynucleotide sequence encoding human miR-9 |
| GGAGGCCCGTTTCTCTCTTTGGTT ATCTAGCTGTATGAGTGCCACAGA GCCGTCATAAAGCTAGATAACCGA AAGTAGAAATGACTCTCA (SEQ ID NO: 5) | DNA polynucleotide sequence encoding mouse miR-9 |
| CGTGTTCACAGCGGACCTTGATTT AATGTCATACAATTAAGGCACGCG GTGAATGCCAA (SEQ ID NO: 6) | DNA polynucleotide sequence encoding mouse miR-124 |
| CGTGTTCACAGCGGACCTTGATTT AAATGTCCATACAATTAAGGCACG CGGTGAATGCCAA (SEQ ID NO: 7) | DNA polynucleotide sequence encoding human miR-124 |
| SEQ ID NO: 8 | AAV vector comprising human shPTB, human miR-9 and human miR-124 |

The invention claimed is:

1. A vector comprising at least one coding sequence for shPTB comprising SEQ ID NO:2 or 3, a coding sequence for an miR-9 comprising SEQ ID NO:4 or 5, and a coding sequence for an miR-124 comprising SEQ ID NO:6 or 7.

2. The vector of claim 1, wherein the vector comprises two coding sequences for shPTB.

3. The vector of claim 2, wherein the vector comprises a sequence selected from the group consisting of SEQ ID NO: 1 and 8.

* * * * *